(12) United States Patent
Kobayashi

(10) Patent No.: US 9,340,811 B2
(45) Date of Patent: May 17, 2016

(54) CELLULASE

(71) Applicant: INDEPENDENT ADMINISTRATIVE INSTITUTION, JAPAN AGENCY FOR MARINE-EARTH SCIENCE AND TECHNOLOGY, Yokosuka-shi, Kanagawa (JP)

(72) Inventor: Hideki Kobayashi, Yokosuka (JP)

(73) Assignee: INDEPENDENT ADMINISTRATIVE INSTITUTION, JAPAN AGENCY FOR MARINE-EARTH SCIENCE AND TECHNOLOGY, Yokosuka-shi (JP)

( * ) Notice: Subject to any disclaimer, the term of this patent is extended or adjusted under 35 U.S.C. 154(b) by 0 days.

(21) Appl. No.: 14/383,473

(22) PCT Filed: Mar. 7, 2013

(86) PCT No.: PCT/JP2013/056232
§ 371 (c)(1),
(2) Date: Sep. 5, 2014

(87) PCT Pub. No.: WO2013/133354
PCT Pub. Date: Sep. 12, 2013

(65) Prior Publication Data
US 2015/0050700 A1 Feb. 19, 2015

(30) Foreign Application Priority Data

Mar. 8, 2012 (JP) .................................. 2012-052313

(51) Int. Cl.
*C12P 19/04* (2006.01)
*C12P 19/14* (2006.01)
*C12P 7/10* (2006.01)
*C12N 9/42* (2006.01)
*C12P 7/04* (2006.01)
*C12P 19/02* (2006.01)

(52) U.S. Cl.
CPC .............. *C12P 19/14* (2013.01); *C12N 9/2437* (2013.01); *C12P 7/04* (2013.01); *C12P 7/10* (2013.01); *C12P 19/02* (2013.01); *C12Y 302/01004* (2013.01); *Y02E 50/16* (2013.01); *Y02P 20/52* (2015.11)

(58) Field of Classification Search
CPC ........................................................ C12P 19/04
USPC ........................................................ 435/183
See application file for complete search history.

(56) References Cited

U.S. PATENT DOCUMENTS 4,945,053 A    7/1990  Ito et al.

FOREIGN PATENT DOCUMENTS

| JP | 61-265089 A | 11/1986 |
| JP | 2001-340074 A | 12/2001 |
| JP | 2011-223962 A | 11/2011 |
| WO | WO 2010/060964 A2 | 6/2010 |

OTHER PUBLICATIONS

Creuzet et al., "Purification and characterization of an endoglucanase from a newly isolated thermophilic anaerobic bacterium", Biochimie, vol. 65, 1983, pp. 149-156.
Hamada et al., "Purification, Characterization and Gene Analysis of Exo-Cellulase II (Ex-2) from the White Rot Basidiomycete Irpex Lacteus", Journal of Bioscience and Bioengineering, vol. 87, No. 4, 1999, pp. 442-451.
International Preliminary Report and Patentability and Translation of the Written Opinion of the International Searching Authority (Forms PCT/IB/326, PCT/IB/373 and PCT/ISA/237), dated Sep. 18, 2014, for International Application No. PCT/JP2013/056232.
International Search Report (Form PCT/ISA/210), dated May 14, 2013, for International Application No. PCT/JP2013/056232.
Kobayashi et al., "Digestive enzymes of Hirondellea gigas and component analysis—Is Hirondellea gigas sweet?", BlueEarth 2011, BE11-39, 2 pages.
Kobayashi et al., "The bacterium isolated from Hirondellea gigas (Shinkaioosokoebi)", JAMSTEC J. Deep Res., vol. 17, 2000, pp. 19-22, with an English Abstract.
Kobayashi et al., "The Hadal Amphipod Hirondellea gigas Possessing a Unique Cellulase . . . ", Plos One, vol. 7, Issue 8, Aug. 2012, pp. 1-8.
Treude et al., "Metabolism and decompression tolerance of scavenging lysianassoid deep-sea amphipods", Deep-Sea Research I, vol. 49, 2002, pp. 1281-1289.
Watanabe et al., "A cellulose gene of termite origin", Nature, vol. 394, Jul. 23, 1998, pp. 330-331.

*Primary Examiner* — Maryam Monshipouri
(74) *Attorney, Agent, or Firm* — Birch, Stewart, Kolasch & Birch, LLP

(57) ABSTRACT

The objects of the present invention are to provide a cellulase that has activity to produce glucose by hydrolyzing crystalline cellulose and which is suitable for saccharification of crystalline cellulose, such as wood, by enzymatic method; and a method of producing glucose and alcohol from crystalline cellulose by utilizing the cellulase. The objects are solved by cellulase having exo-cellulase activity to produce glucose as a main product and cellobiose as a by-product by hydrolyzing crystalline cellulose; and a method of producing glucose and alcohol from crystalline cellulose by utilizing the cellulase.

18 Claims, 21 Drawing Sheets

(4 of 21 Drawing Sheet(s) Filed in Color)

SEQUENCE LISTING

<160> NUMBER OF SEQ ID NOS: 17

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
agagtttgat cctggctcag                                          20

<210> SEQ ID NO 2
<211> LENGTH: 19
<212> TYPE: DNA
<213> ORGANISM: Artificial sequence
<220> FEATURE:
<223> OTHER INFORMATION: Primer

<400> SEQUENCE: 2
ggttaccttg ttacgactt                                                        19

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
ttccggttga tccygccgga                                                       20

<210> SEQ ID NO 4
<211> LENGTH: 19
<212> TYPE: DNA
<213> ORGANISM: Artificial sequence
<220> FEATURE:
<223> OTHER INFORMATION: Primer

<400> SEQUENCE: 4
yccggcgttg amtccaatt                                                        19

<210> SEQ ID NO 5
<211> LENGTH: 11
<212> TYPE: PRT
<213> ORGANISM: Hirondellea gigas

<400> SEQUENCE: 5

Thr Pro Pro Met Gly Trp Leu Ala Trp Glu Arg
1               5                   10

<210> SEQ ID NO 6
<211> LENGTH: 19
<212> TYPE: PRT
<213> ORGANISM: Hirondellea gigas

<400> SEQUENCE: 6

Ser Gln Met Ala Leu Trp Ala Ile Met Ala Ala Pro Leu Phe Met Ser
1               5                   10                  15

Asn Asp Leu

<210> SEQ ID NO 7
<211> LENGTH: 15
<212> TYPE: PRT
<213> ORGANISM: Hirondellea gigas

<400> SEQUENCE: 7

Ala Val Ile Ala Val Asn Gln Asp Pro Leu Gly Ile Gln Gly Arg
1               5                   10                  15

<210> SEQ ID NO 8
<211> LENGTH: 197
<212> TYPE: DNA
<213> ORGANISM: Hirondellea gigas

<400> SEQUENCE: 8
atcaggactc atgagttcga agcccgcacc aatcctgtct ccttgcgatg ctctgtaatg          60
ccctaagtag tcgatcggta tgtaaactga gctacagatg cagccgcctc ggtggtgtag        120
tggatagcgc gcgcacgcgc ctgggaactc agaggtccct ggttcgaatc ccacgccagc        180
caccccatgg ggggagt                                                       197

```
<210> SEQ ID NO 9
<211> LENGTH: 30
<212> TYPE: DNA
<213> ORGANISM: Artificial sequence
<220> FEATURE:
<223> OTHER INFORMATION: enzyme

<400> SEQUENCE: 9
acaccgccaa tgggttggct agcttgggag                              30

<210> SEQ ID NO 10
<211> LENGTH: 61
<212> TYPE: DNA
<213> ORGANISM: Artificial sequence
<220> FEATURE:
<223> OTHER INFORMATION: enzyme

<400> SEQUENCE: 10
gatagcgcgc gcacgcgcct gggaactcag aggtccctgg ttcgaatccc acgccagcca    60
c                                                                    61

<210> SEQ ID NO 11
<211> LENGTH: 227
<212> TYPE: DNA
<213> ORGANISM: Artificial sequence
<220> FEATURE:
<223> OTHER INFORMATION: enzyme

<400> SEQUENCE: 11
acaccgccaa tgggttggct agcttgggag atcaggactc atgagttcga agcccgcacc    60
aatcctgtct ccttgcgatg ctctgtaatg ccctaagtag tcgatcggta tgtaaactga   120
gctacagatg cagccgcctc ggtggtgtag tggatagcgc gcgcacgcgc ctgggaactc   180
agaggtccct ggttcgaatc ccacgccagc caccccatgg ggggagt               227

<210> SEQ ID NO 12
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 12
acnccnccna tgggntggyt ngcntggga                                29
```

```
<210> SEQ ID NO 13
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 13
tcccangcna rccancccat nggnggngt                                      29

<210> SEQ ID NO 14
<211> LENGTH: 39
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 14
atggcnytnt gggcnathat ggcngcnccn ytnttyatg                           39

<210> SEQ ID NO 15
```

```
<211> LENGTH: 39
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 15
catraanarn ggngcngcca tdatngccca narngccat                     39

<210> SEQ ID NO 16
<211> LENGTH: 41
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 16
gcngtnathg cngtnaayca rgayccnytn ggnathcarg g                  41
```

```
<210> SEQ ID NO 17
<211> LENGTH: 41
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 17
ccytgdatnc cnarnggrtc ytgrttnacn gcdatnacng c                                41
```

CELLULASE

CROSS-REFERENCE TO RELATED APPLICATIONS

The present application claims priority from Japanese Patent Application No. 2012-052313 filed on Mar. 8, 2012, the entire contents of which are incorporated herein by reference.

TECHNICAL FIELD

The present invention relates to cellulase that has activity to hydrolyze crystalline cellulose, such as sawdust, into glucose.

BACKGROUND ART

Cellulose is one type of hydrocarbon that is the most abundant on the earth. Cellulose is expected to be used as a raw material for producing bioethanol. However, cellulose is macromolecular. Therefore, before cellulose is used as a raw material for producing bioethanol, saccharification is required to turn cellulose into low-molecular-weight saccharides.

As for cellulose saccharification, an acid hydrolysis method, a subcritical water method, and an enzymatic method are known. Among the above methods, the acid hydrolysis method has problems that a reaction tank is damaged by the use of acids, and that the product obtained after the reaction needs to be neutralized, and that saccharides need to be separated from salts after the neutralization. The subcritical water method has problems that a reaction tanks is damaged by subcritical water, and that the reaction proceeds beyond saccharification until cellulose is decomposed into carbon dioxide and water.

Compared with the acid hydrolysis method and the subcritical water method, the enzymatic method has advantages that the impact on a reaction tank is small, and that low-molecular-weight saccharides are obtained as main products, and that the products can be easily separated. The enzymatic method uses cellulase for cellulose saccharification.

Cellulase is a general term for enzymes that catalyze the hydrolysis of cellulose. The known representative examples of cellulase include the following enzymes: cellulase (EC 3.2.1.4), cellulose 1,4-β-cellobiosidase (EC 3.2.1.91), and β-glucosidase (EC 3.2.1.21). Among the above enzymes, cellulase is also referred to as endo-cellulase; cellulose 1,4-β-cellobiosidase is also referred to as cellobiohydrolase.

Some of invertebrates such as termites use cellulase, which is synthesized in their bodies, to assimilate wood. However, when only a single cellulase is used, it is difficult to extract nutrients from the wood. Therefore, scavengers such as termites make use of three types of cellulase (See Non-Patent Document 1 below, the contents of which are incorporated herein by reference). That is, those three types are: endo-cellulase that catalyzes the hydrolysis of cellulose molecules into cellooligosaccharides; cellobiohydrolase that catalyzes the hydrolysis of cellooligosaccharides into cellobiose; and β-glucosidase that catalyzes the hydrolysis of cellobiose into glucose.

The use of a mixture of the three types of cellulase, i.e. endo-cellulase, cellobiohydrolase, and β-glucosidase, makes it theoretically possible to consistently produce glucose from crystalline cellulose such as wood. However, such glucose consistent production has yet to be put into practical use.

In general, if a mixture of two or more purified enzymes is employed, the following conditions need to apply: Condition 1 in which the reaction products of each enzyme do not inhibit the reaction of the other enzymes; and Condition 2 in which the optimum temperatures and optimum pHs of each enzyme need to be consistent. However, endo-cellulase is inhibited by cellobiose and glucose, which are reaction products of cellobiohydrolase and β-glucosidase. Moreover, cellobiohydrolase is inhibited by glucose, which is a reaction product of β-glucosidase. Accordingly, if the mixture of the three types of cellulase, i.e. endo-cellulase, cellobiohydrolase, and β-glucosidase, is used for cellulose saccharification, the above Condition 1 cannot be satisfied (See Non-Patent Document 2 below, the contents of which are incorporated herein by reference).

In view of the above Condition 1, it is hoped that endo-cellulase produced by alkalophilic bacteria, which is not inhibited by cellobiose, will be used (See Patent Document 1 below, the contents of which are incorporated herein by reference). However, the optimum pH of the endo-cellulase derived from alkalophilic bacteria is close to the alkaline side. Therefore, if the reaction takes place under alkaline conditions in line with such a property of alkaline endo-cellulaseendo-cellulase, cellooligosaccharides, which are reaction products of the endo-cellulaseendo-cellulase, are isomerized. As a result, the substrate of cellobiohydrolase, which is to be subjected to a subsequent reaction, is inappropriate. Moreover, the activity of typical β-glucosidase is low under alkaline conditions. Accordingly, if the endo-cellulase derived from alkalophilic bacteria is use to meet the above Condition 1, then the above Condition 2 will not become satisfied.

There has not yet been a mixture of endo-cellulase, cellobiohydrolase, and β-glucosidase that would satisfy the above Conditions 1 and 2. Accordingly, a process of consistently producing glucose from natural cellulose such as wood by using the three types of cellulase has not yet been realized. Meanwhile, attempts have been made to carry out saccharification of natural cellulose such as wood in a single enzyme system by using cellulase that has activity to hydrolyze non-crystalline cellulose molecules (See Patent Documents 2 and 3 below, the contents of which are incorporated herein by reference).

As a scavenger that can assimilate, like termites, wood by utilizing cellulase, the amphipod Hirondellea gigas is known (See Non-Patent Document 3 below, the contents of which are incorporated herein by reference). Hirondellea gigas is one type of gammaridean amphipods that live in the world's deepest part of the Challenger Deep in the Mariana Trench. The research on Hirondellea gigas became popular after unmanned probe "Kaiko" succeeded in capturing more than 100 individuals of Hirondellea gigas in 1998 (See Non-Patent Document 4 below, the contents of which are incorporated herein by reference).

The crushed products of Hirondellea gigas have so far been known to have the activity of protease, α-glucosidase, lipase, amylase, cellulase, and glucomannan degrading enzyme. However, there are no reports that those enzymes have been individually isolated (See Non-Patent Document 5 below, the contents of which are incorporated herein by reference).

PRIOR ART DOCUMENTS

Patent Documents

[Patent Document 1] Japanese Patent Application Publication (KOUKAI) No. 2001-340074
[Patent Document 2] Japanese Patent Application Laid-Open Publication (KOUKAI) No. S63-109778

[Patent Document 3] Japanese Patent Application Laid-Open Publication (KOUKAI) No. 2011-223962

Non-Patent Documents

Non-Patent Document 1: Watanabe, H. et al., Nature, 394, 330-331 (1998)
Non-Patent Document 2: NicoleCreuzet et al, Biochimie, 65, 149-156 (1983)
Non-Patent Document 3: T. Treude et al., Deep Sea Res. Part I Oceanogr. Res. Pap. 49, 1281-1289 (2002)
Non-Patent Document 4: H. Kobayashi et al., JAMSTEC J. Deep Res. 17, 19-22 (2000)
Non-Patent Document 5: Hideki Kobayashi et al., "Digestive enzymes of Hirondellea gigas and component analysis—Is Hirondellea gigas sweet?"-BlueEarth 2011, BE11-39

DISCLOSURE OF THE INVENTION

Problems to be Solved by the Invention

It appears to be possible to carry out saccharification of non-crystalline cellulose if cellulase disclosed in Patent Documents 2 and 3 is used. However, Patent Document 2 states that CMC-ase II disclosed in Patent Document 2 has a slight $C_1$ activity, and that, when Avicel, which is crystalline cellulose, or pieces of filter paper were used as substrate, the evaluation index for substrate specificity was reducing sugar, not glucose (See Patent Document 2; line 20 in the upper right column on page 7 to line 2 in the lower left column). In general, the reducing sugar includes not only glucose but also other oligosaccharides like disaccharides, trisaccharides, and tetrasaccharides. The amount of reducing sugar produced was 0.3 percent or less of the amount of glucose produced at the time when carboxymethyl cellulose (CMC), which is non-crystalline cellulose, was used as substrate (See Table 1 in Patent Document 2).

Given the above facts, CMC-ase II disclosed in Patent Document 2 cannot substantially decompose crystalline cellulose. Even if crystalline cellulose can be decomposed, what is produced is not only glucose but also a variety of reducing sugars. Therefore, the probability is high that the activity thereof is an endo-cellulase activity that enables hydrolysis of crystalline cellulose within a molecule thereof. If that is the case, CMC-ase II disclosed in Patent Document 2 may be able to hydrolyze crystalline cellulose, but the probability is very high that glucose is not produced.

Similarly, Patent Document 3 states that $CMC1\text{-}CBD_{CBHI}$ disclosed in Patent Document 3 is able to hydrolyze Avicel, which is crystalline cellulose (See Table 13 in Patent Document 3). However, Patent Document 3 discloses that the product detected is reducing sugar, not glucose (See paragraph 0127 in Patent Document 3). Moreover, only the $CBD_{CBHI}$ portion of $CMC1\text{-}CBD_{CBHI}$ shows an exo-cellulase activity. However, according to paragraph 0004 of Patent Document 3, CBH (cellobiohydrolase) has the activity to produce cellobiose, which is disaccharide. Accordingly, even if $CMC1\text{-}CBD_{CBHI}$ disclosed in Patent Document 3 is applied to crystalline cellulose, the reducing sugar mainly produced is cellobiose, not glucose.

Meanwhile, Non-Patent Document 5 was described by the inventor and other fellow researchers. Non-Patent Document 5 does not disclose what kind of enzymes the cellulase activity exhibited by the crushed product of Hirondellea gigas has been dependent on. The cellulase activity of the crushed product of Hirondellea gigas is actually measured with AZO-CM-Cellulose (Megazyme) as an endo-cellulase activity. In this manner, when Non-Patent Document 5 was released, the cellulase activity that the crushed product of Hirondellea gigas had was recognized as an endo-cellulase activity that hydrolyzed non-crystalline cellulose from inside a molecule.

As described above, the cellulase disclosed in Patent Documents 2 and 3 has the activity to hydrolyze crystalline cellulose. However, the main products are oligosaccharides such as cellobiose, and the probability is high that glucose is not produced. Moreover, the cellulase activity that the Hirondellea gigas extract disclosed in Non-Patent Document 5 had was measured as an endo-cellulase activity. Accordingly, even if the cellulase disclosed in Patent Documents 2 and 3 and the Hirondellea gigas extract disclosed in Non-Patent Document 5 are used, it is effectively impossible to obtain glucose as a main product by using crystalline cellulose, such as wood, as substrate.

Therefore, the first object of the present invention is to provide cellulase that has activity to produce glucose by hydrolyzing crystalline cellulose and which is suitable for saccharification of crystalline cellulose, such as wood, by enzymatic method. The second and third objects of the present invention are to provide a method of producing glucose and alcohol from crystalline cellulose by utilizing the enzyme of the present invention.

Means of Solving the Problems

To achieve the above objects, the inventors intensively studied cellulase having the activity to hydrolyze crystalline cellulose. The inventors eventually focused on cellulase that Hirondellea gigas has.

In order to isolate an enzyme having a cellulase activity from Hirondellea gigas, the inventors disassembled Hirondellea gigas, and removed outer shells. Then, the inventors crushed Hirondellea gigas using a commercially-available hand-rubbing-type simple crushing container. Then, the crushed product of one individual of Hirondellea gigas was immersed three times in 1 mL of distilled water. As a result, 3 mL of a protein extraction solution was obtained in total. Then, ammonium sulfate was added so that the final concentration of the protein extraction solution came to 80% (saturation %) (ammonium sulfate precipitation). As a result, all proteins in the protein extraction solution were precipitated. Then, the precipitated proteins were dissolved in 1 mL of distilled water, and were desalted and concentrated by using an ultrafiltration column. As a result, 0.2 mL of a protein concentrated solution was obtained.

The protein concentrated solution thus obtained showed an endo-cellulase activity. However, at the same time, the protein concentrated solution showed the activities of protease, α-glucosidase, lipase, amylase, cellulase, and glucomannan degrading enzyme. That is, the protein concentrated solution was a solution that contains all enzymes inside the body of Hirondellea gigas.

Moreover, the inventors carried out an ammonium sulfate fractionation with varying concentrations of ammonium sulfate in the course of ammonium sulfate precipitation. In a fraction where ammonium sulfate was 50 to 60% (saturation %), all components in the protein extraction solution were precipitated. Therefore, a fraction showing only a cellulase activity could not be obtained. This is considered attributable to the fact that, because Hirondellea gigas was a hadal organism and therefore contained large amounts of lipid and oil, the use of the above-described normal protein extraction method led to the simultaneous extractions of not only proteins such as enzymes but also lipid, oil, body fluids, and the like in the body of Hirondellea gigas and the formation of emulsion.

The inventors tried to isolate cellulase from the protein concentrated solution by forcing the protein concentrated solution through ion-exchange chromatography, which used an anion or cation exchange resin, or through hydrophobic chromatography, which used a hydrophobic resin containing a butyl group or a phenyl group. However, the ion-exchange resin could not absorb protein in an effective range thereof (pH 3 to 10). Moreover, the protein adsorbed by the hydrophobic resin could not be eluted even as 4M NaCl was added. Accordingly, since the hydrophobicity of the emulsion of the protein concentrated solution was very high, the peripheries of all proteins containing cellulase were considered to be covered with lipid and oil. Therefore, it was very difficult to isolate a specific protein (enzyme) in the protein concentrated solution.

The inventors then assumed that, if Hirondellea gigas was left at room temperatures, the oil inside the body of Hirondellea gigas would help force cellulase out of the body together with body fluids. However, from an extraction solution that was obtained after Hirondellea gigas was left in water at room temperatures, a cellulase activity could not be detected. Accordingly, the inventors decided to add a protease inhibitor based on the assumption that the cellulase eluted out of the body was decomposed by protease inside the body of Hirondellea gigas. However, a cellulase activity could not be detected, as is the case with no addition of protease.

The inventors carried out various experiments and studies, through a trial and error process, as to how to isolate cellulase in the body of Hirondellea gigas. As a result, the inventors succeeded in obtaining a purified cellulase, HGcel, by using a method described later in examples. Surprisingly, HGcel shows an exo-cellulase activity, not an endo-cellulase activity detected in Non-Patent Document 5; can produce glucose as a main product by hydrolyzing crystalline cellulose; and can produce cellobiose as a by-product. The present invention has been completed based on the results of research in which the inventors have isolated HGcel from Hirondellea gigas for the first time, and unveiled the physicochemical properties of HGcel as described above.

According to the present invention, what is provided is cellulase having an exo-cellulase activity to produce glucose as a main product by hydrolyzing crystalline cellulose.

Preferably, the cellulase has an exo-cellulase activity to produce cellobiose as a by-product by hydrolyzing crystalline cellulose.

Preferably, the cellulase has activity to produce glucose as a main product by hydrolyzing non-crystalline cellulose, and an amount of glucose produced by hydrolyzing crystalline cellulose is one-hundredth or more than an amount of glucose produced by hydrolyzing non-crystalline cellulose.

Preferably, the cellulase has activity to produce 1 μg/mL or more of glucose as a main product by hydrolyzing 5% (w/v) sawdust in a sodium acetate buffer solution (pH 5.6) under reaction conditions of 35 degrees Celsius and 5 hours.

Preferably, a molar ratio of glucose, which is a main product, and cellobiose, which is a by-product, is 1.5:1 to 2.5:1.

Preferably, the crystalline cellulose is selected from a group consisting of sawdust, paper, fiber, wood and Avicel as well as stalk, root, petal and leaf of plant.

Preferably, the non-crystalline cellulose is selected from a group consisting of carboxymethyl cellulose, phosphoric acid swollen cellulose, alkali swollen cellulose, and sodium cellulose xanthate.

Preferably, the cellulase is cellulase derived from Hirondellea gigas.

Preferably, the cellulase has a molecular weight of 55,000 to 63,000 by SDS-PAGE method.

Preferably, the cellulase has an optimum pH of 5.4 to 5.8.

Preferably, the cellulase has an optimum temperature of 25 to 40 degrees Celsius.

Preferably, the cellulase comprises an amino acid sequence encoded by a base sequence disclosed in SEQ ID No. 8 or a base sequence that hybridizes with a base sequence complementary to the base sequence under stringent conditions.

According to another aspect of the present invention, what is provided is a method of producing glucose, comprising a step of producing glucose as a main product through a reaction of crystalline cellulose and/or non-crystalline cellulose with the cellulase of the present invention.

According to another aspect of the present invention, what is provided is a method of producing alcohol, comprising: a step of producing glucose as a main product through a reaction of crystalline cellulose and/or non-crystalline cellulose with the cellulase of the present invention; and a step of producing alcohol by fermenting the produced glucose.

Effects of the Invention

Saccharification carried out by the enzymatic method for natural cellulose, such as wood, becomes easier and faster as the types of enzymes to be used are less. The cellulase of the present invention is in line with this concept. The cellulase of the present invention can convert natural cellulose into glucose by itself. Moreover, the cellulase of the present invention can convert natural cellulose into glucose and cellobiose, which both can be assimilated by microorganisms or the like. Therefore, by utilizing a reaction solution obtained through a reaction of the cellulase of the present invention with natural cellulose, it is possible to very efficiently produce bioethanol by fermentation method.

Moreover, the cellulase of the present invention can hydrolyze crystalline cellulose. Therefore, without the use of corn, sugar cane or the like, that is valuable as food, glucose and alcohol can be produced from non-food crops, stems of corn or sugar cane, waste material, and the like. This proves that the production of glucose and alcohol by the use of the cellulase of the present invention is economically excellent, and, in particular, glucose and alcohol can be expected to be produced on an industrial scale.

An optimum reaction temperature of HGcel, which is one specific embodiment of the cellulase of the present invention, is low. Therefore, without the need for heating, an enzymatic reaction can take place. Therefore, glucose can be produced in an energy-saving manner. Furthermore, a typical culture temperature of yeast used for ethanol fermentation overlaps with the optimum reaction temperature of HGcel. Therefore, the production of glucose and bioethanol can take place in the same system without the need to change temperatures.

Timbers contain hemicellulose, such as cellulose, mannan, or xylan, and lignin. Accordingly, before wood derived from timbers were processed by conventional endo-cellulase, the destruction of the crystal structure of cellulose, including removal of lignin by alkali treatment, has been required in advance. However, the cellulase of the present invention has the activity to hydrolyze a non-reducing end of a cellulose molecule. Therefore, according to the cellulase of the present invention, glucose can be more easily produced from sawdust, which is generated during processing of timbers, without the need for preliminary treatment of timbers such as alkali treatment.

BRIEF DESCRIPTION OF THE DRAWING

The patent or application file contains at least color drawings. Copies of this patent or patent application publication with color drawings will be provided by the USPTO upon request and payment of the necessary fee.

MODE FOR CARRYING OUT THE INVENTION

Figure 1A:
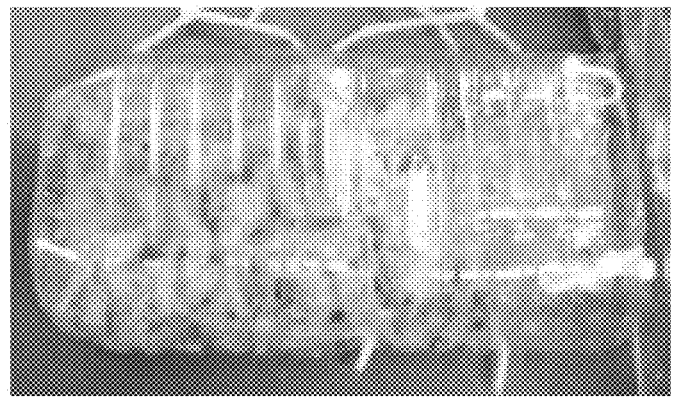
FIG. 1a is a diagram showing one example of a baited trap, which contains about 50 individuals of Hirondellea gigas.

Hereinafter, the present invention is described in detail. Cellulase of the present invention acts on both crystalline cellulose and non-crystalline cellulose, and has an exo-cellulase activity to produce glucose as a main product and cellobiose as a by-product.

The cellulase of the present invention is an enzyme that catalyzes the hydrolysis of cellulose, and is similar to other kinds of cellulase in that regard. However, unlike other kinds of cellulase, the cellulase of the present invention has a unique activity to act on not only non-crystalline cellulose such as carboxymethyl cellulose (CMC) but also on crystalline cellulose such as sawdust and Avicel and to produce glucose as a main product.

The term "main product" herein means those with the highest molar concentration out of saccharides that are produced through a reaction of cellulase with cellulose. The term "by-product" herein means those with the second highest molar concentration out of saccharides that are produced through a reaction of cellulase with cellulose.

One of the reasons why the cellulase of the present invention can act on crystalline cellulose to produce glucose and cellobiose is presumed to be that the cellulase of the present invention includes a domain binding to the crystalline cellulose, and the activity thereof is exo-cellulase activity. Therefore, the cellulase of the present invention is considered to be able to adhere to crystalline cellulose, and hydrolyze an end portion of crystalline cellulose to release glucose and cellobiose. However, the structure of HGcel, which is one specific embodiment of the cellulase of the present invention, is still unclear due to various problems. Therefore, it is impossible to definitively determine what the above presumption and consideration are. This cannot be a reason for a narrower interpretation of the technical scope of the present invention.

The crystalline cellulose and non-crystalline cellulose on which the cellulase of the present invention acts are not specifically limited. In this specification, crystalline cellulose is those in which the ratio of crystalline portion in a cellulose molecule is relatively larger, and is roughly over 10% (w/w).

In this specification, cellulose other than crystalline cellulose is referred to as non-crystalline cellulose. Specific examples of crystalline cellulose on which the cellulase of the present invention acts include: sawdust, paper, fiber, wood and Avicel, as well as the stalk, root, petal and leaf of plant, and other kinds of natural cellulose that exist in the natural world; and artificial cellulose, such as those artificially synthesized, chemically modified, or processed. Specific examples of non-crystalline cellulose on which the cellulase of the present invention acts include: carboxymethyl cellulose, phosphoric acid swollen cellulose, alkali swollen cellulose, and sodium cellulose xanthate.

The cellulase of the present invention can produce glucose by hydrolyzing cellulose material including crystalline cellulose and non-crystalline cellulose. However, even in the case of the same concentration (percent concentration of weight (mass)), the glucose content may vary according to the type of the cellulose material. For example, the amount of glucose that the cellulase of the present invention produces by hydrolyzing crystalline cellulose may be smaller than the amount of glucose that the cellulase of the present invention produces by hydrolyzing non-crystalline cellulose, or, more specifically, may be one-hundredth or more of the amount. The amount of glucose that HGCel, which is one specific embodiment of the cellulase of the present invention, produces by hydrolyzing 5% (w/v) sawdust is about one-fifth of the amount of glucose that HGcel produces by hydrolyzing 5% (w/v) carboxymethylcellulose.

The intensity of the activity of the cellulase of the present invention is affected by the type of substrate and reaction conditions, and is therefore not specifically limited. For example, in the case of hydrolyzing 5% (w/v) sawdust in a sodium acetate buffer solution (pH 5.6), under reaction conditions of 35 degrees Celsius and 5 hours, The intensity of the activity is defined by the amount (concentration) of glucose produced as a main product wherein the amount is 1 µg/mL or more, or preferably 5 µg/mL or more, or more preferably 10 µg/mL or more, or even more preferably 15 µg/mL or more.

The cellulase of the present invention produces glucose as a main product and cellobiose as a by-product, even as one of the cellulose materials, including crystalline cellulose and non-crystalline cellulose, is used as substrate. The molar ratio of the produced glucose and cellobiose is not specifically limited. For example, the molar ratio is 1.5:1 to 2.5:1, or preferably 1.8:1 to 2.2:1, or more preferably 2:1.

The cellulase of the present invention is a very revolutionary enzyme as the cellulase can produce glucose by itself by acting on crystalline cellulose and non-crystalline cellulose. As a method of using the cellulase of the present invention in such a way as to make use of the above properties, for example, what is available includes a method comprising the steps of: preparing a cellulose sample solution by adding cellulose material, such as sawdust produced during cutting of wood or commercially-available copy paper, to a buffer solution whose pH has been adjusted in such a way as to be suitable for the cellulase of the present invention; adding the cellulase of the present invention to the sample solution; and producing glucose through a reaction of the cellulase of the present invention with the cellulose material at a temperature suitable for the cellulase of the present invention. For example, another method available comprises the steps of: dripping, on cellulose material, an enzyme solution, which is prepared by adding the cellulase of the present invention to a buffer solution whose pH has been adjusted in such a way as to be suitable for the cellulase of the present invention; keeping a temperature suitable for the cellulase of the present invention; and producing glucose in an area of the cellulose material on which the enzyme solution was dripped. In this manner, as the method of using the cellulase of the present invention, a method of producing glucose from all or part of the cellulose material is available.

Unless otherwise specified, the exo-cellulase activity of the cellulase of the present invention can be determined after the cellulase of the present invention and the cellulose material are suspended in a buffer solution with pH adjusted to 5.6 in such a way that the concentration thereof becomes appropriate, and the reaction of both takes place at 35 degrees Celsius followed by the concentration of glucose and cellobiose in the aqueous phase of the reaction system being detected. The concentration of glucose may be measured by Glucose CII kit (Wako Pure Chemical Industries, Ltd.). The concentration of cellobiose can be calculated by measuring the glucose concentration after 1 U β-glucosidase (Oriental Yeast Co., Ltd.) is added to the above reacted solution and a reaction takes place 37 degrees Celsius for 16 hours. According to the present invention, one unit of cellulase activity is defined as being able to produce 1 µg per minute of glucose by hydrolyzing the cellulose material. When natural cellulose is used as the cellulose material, it is desirable that the natural cellulose be washed, sterilized, or dried in advance by an appropriate method in order to prevent contamination caused by bacteria or the like adhering to the natural cellulose.

One specific embodiment of the cellulase of the present invention is HGcel, which will be described later in examples. Hereinafter, the physicochemical properties that a preferred embodiment of the cellulase of the present invention has will be described in reference to the physicochemical properties of HGcel.

Since the optimum pH of the cellulase of the present invention may have an effect on the crystalline structure and the like of cellulose material that is substrate under alkaline conditions, the optimum pH is preferably in an acidic-to-neutral range. For example, the optimum pH is between 4.0 and 8.0, or more preferably between 4.5 and 7.5, or even more preferably between 5.0 and 7.0. The optimum pH of HGcel, which is a specific embodiment of the cellulase of the present invention, is between 5.4 and 5.8.

In the case wherein cellulase activity is measured, and the pH of a cellulose substrate solution is changed by the use of a sodium acetate buffer solution, a citrate buffer solution, a MES buffer solution, a sodium phosphate buffer solution, a glycylglycine buffer solution, a TABS buffer solution, or the like, the "optimum pH" herein is the pH where relative activity of 80% or more is observed against the 100% of the cellulase activity at a time when the pH thereof is set to 5.6 and the temperature is set to 35 degrees Celsius.

The optimum temperature of the cellulase of the present invention is preferably a temperature suitable for reaction under normal temperatures. For example, the optimum temperature is between 0 degrees Celsius and 60 degrees Celsius, or more preferably between 10 degrees Celsius and 50 degrees Celsius, or even more preferably 20 degrees Celsius and 40 degrees Celsius. The optimum temperature of HGcel, which is a specific embodiment of the cellulase of the present invention, is between 25 degrees Celsius and 35 degrees Celsius.

When the temperature where the reaction of a mixed buffer solution (pH 5.6) containing the cellulase of the present invention and the cellulose material takes place is changed, the "optimum temperature" herein is the temperature where relative activity of 80% or more is observed against the 100% of cellulase activity at a time when the temperature thereof is set to 35 degrees Celsius.

Since the cellulase of the present invention should preferably be suitable for reaction under normal temperatures, the temperature stability of the cellulase of the present invention is, for example, between 0 degrees Celsius and 60 degrees Celsius, or more preferably 0 degrees Celsius and 50 degrees Celsius, or even more preferably 0 degrees Celsius and 40 degrees Celsius. The temperature stability of HGcel, which is a specific embodiment of the cellulase of the present invention, is between 0 and 35 degrees Celsius.

The "temperature stability" herein is a temperature where the remaining activity of the cellulase of the present invention is 80% or more. As for the cellulase of the present invention, if the remaining activity is measured under varying temperature conditions, based on a value of the cellulase activity measured immediately after a freeze-preserved enzyme is thawed, the cellulase activity is measured after 2-hour incubation at each temperature, and then the remaining activity is measured based on the ratio of those activity values.

The molecular weight of the cellulase of the present invention is not specifically limited. In terms of the molecular weight of HGcel, for example, the molecular weight by SDS-PAGE method is preferably between 55,000 and 63,000. Incidentally, the molecular weight of HGcel is about 59,000.

The cellulase of the present invention can be obtained by analyzing and evaluating substances inside or outside bodies of various organisms, such as saprophagous microorganisms, invertebrates, and vertebrates, or preferably gammaridean amphipods, which are saprophagous amphipods, with the use of indicators including the optimum pH, optimum temperature, molecular weight, and other factors of HGcel, which is a specific embodiment of the cellulase of the present invention, as well as the above cellulase activity.

A preferred organism from which the cellulase of the present invention is produced is Hirondellea gigas. The method of isolating the cellulase of the present invention from Hirondellea gigas is not specifically limited. For example, the method described later in examples is available.

In order to obtain the cellulase of the present invention from any organism other than Hirondellea gigas, the internal sequences of HGcel disclosed in SEQ ID NO: 5 to 7 are used as indicators. The cellulase of the present invention can be obtained from enzyme extract of the organism with the use of bioengineering techniques such as western blotting.

The base sequence disclosed in SEQ ID NO: 8 (ATCAG-GACTCATGAGTTCGAAGCCCGCACCAATCCTGTCT-CCTTGCGATGCTCTGTAATGCCCTAAGTAGTCGATC-GGTATGTAAACTGAGCTACAGATGCAGCCGCCTCG-GTGGTGTAGTGGATAGCGCGCGCACGCGCCTGGG-AACTCAGAGGTCCCTGGTTCGAATCCCACGCCAGC-CACCCCATGGGGGAGT) is a base sequence that encodes an amino acid sequence that is considered to be part of an amino acid sequence of HGcel. Moreover, HGcel is considered to include, in an upstream portion of the base sequence disclosed in SEQ ID NO: 8, a base sequence that encodes an amino acid sequence that is homologous to a part of a conserved region of α-glucosidase; the amino acid sequence is an amino acid sequence encoded by: ACACCGC-CAATGGGTTGGCTAGCTTGGGAG (SEQ ID NO: 9). Furthermore, HGcel is considered to include abase sequence that encodes an amino acid sequence that is homologous to a part of a domain region of cellobiohydrolase (GAT-AGCGCGCGCACGCGCCTGGGAACTCA-GAGGTCCCTGGTTCGAATCCCACGCCAGCCAC; SEQ ID NO: 10). In this manner, HGcel is presumed to include a part of α-glucosidase and a part of cellobiohydrolase, and therefore has a very specific amino acid sequence.

As for the base sequence disclosed in SEQ ID NO: 11 (ACACCGCCAATGGGTTGGCTAGCTTGGGAGATCA-GGACTCATGAGTTCGAAGCCCGCACCAATCCTGTC-TCCTTGCGATGCTCTGTAATGCCCTAAGTAGTCGA-TCGGTATGTAAACTGAGCTACAGATGCAGCCGCCT-CGGTGGTGTAGTGGATAGCGCGCGCACGCGCCTG-GGAACTCAGAGGTCCCTGGTTCGAATCCCAC GCCAGCCACCCCATGGGGGGAGT), which is made by adding the base sequence of SEQ ID NO: 9 to an upstream portion of the base sequence disclosed in SEQ ID NO: 8, a homology search (Identities) is carried out using the BLAST search after the $1^{st}$ position "A" is removed. The result is that the saccharide degrading enzyme with the highest identity is 1,4-beta cellobiohydrolase [Micromonospora aurantiaca ATCC27029]; the identity thereof is about 52% (11/21 amino acid sequence).

The base sequence that encodes HGcel is a unique base sequence that encodes a part of α-glucosidase and a part of cellobiohydrolase. Therefore, the probability is high that the following protein is cellulase of the present invention: the protein that is derived from gammaridean amphipods and includes an amino acid sequence encoded by a base sequence that hybridizes under stringent conditions with a DNA fragment containing a base sequence complementary to a base sequence made up of the 50 or more consecutive bases, or preferably 100 or more consecutive bases, or more preferably 150 or more consecutive bases, or even more preferably 180 or more consecutive bases, of the base sequence disclosed in SEQ ID NO: 8.

The sentence "hybridizes under stringent conditions" herein means a base sequence of the DNA that is obtained by using a colony hybridization method, a plaque hybridization method, a southern blot hybridization method or the like with the use of DNA as a probe. For example, the DNA includes those identified by, with the use of a filter on which a colony-derived or plaque-derived DNA or a fragment of the DNA is fixed, subjecting to hybridization at 40 to 75 degrees Celsius in the presence of 0.5 to 2.0M NaCl, or preferably hybridization at 65 degrees Celsius in the presence of 0.7 to 1.0M NaCl followed by washing the filter under a condition of 65 degrees Celsius with the use of a 0.1 to 2×SSC solution (a 1×SSC solution contains 150 mM of sodium chloride and 15 mM of sodium citrate). The above sentence means this DNA or the like. The preparation and hybridization of the probe may be performed in accordance with the method disclosed in the following document or the like (The contents of those documents are incorporated herein by reference): Molecular Cloning: A laboratory Manual, 2nd Ed., Cold Spring Harbor Laboratory, Cold Spring Harbor, N.Y., 1989, Current Protocols in Molecular Biology, Supplement 1 to 38, John Wiley & Sons (1987-1997). Incidentally, a person of ordinary skill in the art may be able to set conditions for obtaining a base sequence that encodes the cellulase of the present invention by taking into account various other conditions such as probe concentration, probe length, and reaction time, in addition to such conditions as the salt concentration and temperature of the buffer.

The DNA fragment comprising a base sequence that hybridizes under stringent conditions includes DNA having a certain degree of homology (identity) with a base sequence of DNA that is used as a probe. For example, what is available is a DNA fragment having an identity of 70% or more, or preferably an identity of 80% or more, or more preferably an identity of 90% or more, or even more preferably an identity of 95% or more, or still more preferably an identity of 98% or more.

For example, the base sequences that hybridize under stringent conditions with a base sequence complementary to the base sequence disclosed in SEQ ID NO: 8 or 11 include: base sequences with deletion, replacement, and/or addition of one to several bases, or preferably 1 to 50 bases, or more preferably 1 to 30 bases, or even more preferably 1 to 20 bases, or still more preferably 1, 2, 3, 4, 5, 6, 7, 8, 9, or 10 bases, in the base sequence disclosed in SEQ ID NO: 8 or 11.

The phrase "deletion of a base" means that the base in the sequence is deleted or lost. The phrase "replacement of a base" means that the base in the sequence is replaced with another base. The phrase "addition of a base" means that the base is added.

For example, the process of determining whether or not a protein comprising amino acids encoded by a base sequence that hybridizes under stringent conditions with a base sequence complementary to the base sequence disclosed in SEQ ID NO: 8 or 11 has an exo-cellulase activity that the cellulase of the present invention has comprises the steps of: preparing a recombinant vector that is joined to a drug resistance gene and a base sequence that hybridizes under stringent conditions with a base sequence complementary to the base sequence disclosed in SEQ ID NO: 8 or 11; producing a transformant by introducing the recombinant vector into a host body; culturing the transformant in the presence of a drug corresponding to the drug resistance gene; and then determining the existence of a protein having a cellulase activity from the transformant and the culture solution.

According to another aspect of the present invention, what is provided is a method of producing glucose by the use of the cellulase of the present invention. The method of producing glucose of the present invention is not specifically limited as long as the method comprises a step of producing glucose as a main product through a reaction of crystalline cellulose or non-crystalline cellulose, or both crystalline cellulose and non-crystalline cellulose, with the cellulase of the present invention.

Although not specifically limited, specific embodiments of the method of producing glucose of the present invention include the method comprising the steps of: washing and sterilizing sawdust and then drying the sawdust; adding the dried sawdust and an enzyme preparation solution containing the cellulase of the present invention to a sodium acetate buffer solution (pH 5.6); subjecting to a reaction at 25 to 35 degrees Celsius from a few hours to several tens of hours to obtain a cellulase reaction solution; adding β-glucosidase to the cellulase reaction solution; and subjecting to the reaction from a few hours to several tens of hours under conditions suitable for the activity of β-glucosidase to obtain a glucosidase reaction solution. Furthermore, if necessary, solid glucose may be obtained by drying the glucosidase reaction solution obtained; or a glucose concentrated solution may be obtained by performing a glucose separation method that is commonly known to a person of ordinary skill in the art, such as a chromatography method, or by performing a concentration method.

According to another aspect of the present invention, what is provided is a method of producing alcohol with the use of the cellulase of the present invention or the method of producing glucose of the present invention. The method of producing alcohol of the present invention is not specifically limited as long as the method comprises a step of producing glucose as a main product through a reaction of crystalline cellulose or non-crystalline cellulose, or both crystalline cellulose and non-crystalline cellulose, with the cellulase of the present invention, and a step of producing alcohol by fermenting the produced glucose.

As for the step of producing alcohol by fermenting the glucose, an alcohol fermentation method that is commonly known to a person of ordinary skill in the art may be applied, and the step is not specifically limited. For example, the step can be performed by adding, to the solution obtained by the glucose production step, yeast (*S. cerevisiae, S. pombe* or the like) suitable for alcohol fermentation and nutrients; and by carrying out proliferation and fermentation in two stages under culture conditions that are suitable for the yeast to be used, or by continuously culturing anaerobically or aerobically. The type of alcohol to be produced is not specifically limited. Preferably, ethanol is produced.

The cellulase of the present invention can be comprised in a glucose production kit together with a buffer solution of pH 5.4 to 5.8 suitable for the cellulase of the present invention. The buffer solution of pH 5.4 to 5.8 is not specifically limited. For example, the following solutions may be available: a sodium acetate buffer solution of pH 5.4 to 5.8; a MES buffer solution of pH 5.4 to 5.8; a citrate buffer solution of pH 5.4 to 5.8; and a citric acid—phosphate buffer solution of pH 5.4 to 5.8.

In the kit containing the cellulase of the present invention, the cellulase of the present invention and a buffer solution of pH 5.4 to 5.8 may be separately packaged, or may be packaged after being mixed.

The order that components of the kit containing the cellulase of the present invention are added to cellulose material is not specifically limited. If the components are separately packaged, the cellulase of the present invention may be added after the cellulose material is added to a buffer solution of pH 5.4 to 5.8; or the cellulose material may be added after the cellulase of the present invention is added to a buffer solution of pH 5.4 to 5.8.

Hereinafter, the present invention will be explained in more detail by using examples. However, the present invention is not limited to the examples.

EXAMPLES

1. Materials and Methods
(1) Capturing of Hirondellea gigas

Figure 4A:
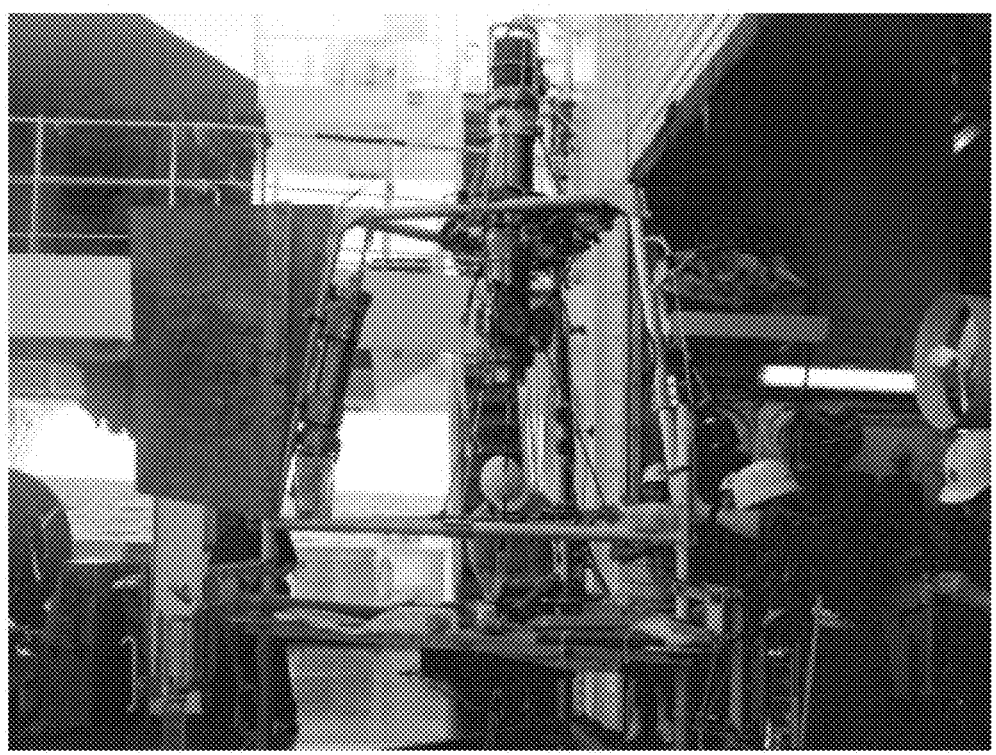
FIG. 4a is a diagram showing a 10,000 m-class free-fall camera sediment sampler system "Ashura (ASHURA)"; ASHURA are equipped with a camera and three core samplers to collect soil samples; ASHURA was sent down into the bottom of the Challenger Deep, and the position thereof was traced by sonar.
Figure 4B:
FIG. 4b is a diagram showing traps with bait that are attached to side bars; three traps with bait are attached to the side bars; the traps with bait contain mackerel fillets.

A 11,000 m-class camera system (ASHURA) to which four baited traps were attached was prepared. The baited traps were sent down in such a way as to reach the deepest point of the Mariana Trench for 2.5 hours (Latitude 11°22.11'N, Longitude 142°25.86'E, Depth 10,897 m) (See FIGS. 4a and 4b). Only 185 individuals of amphipods (Hirondellea gigas) were captured. Hirondellea gigas was stored in a −80 degree Celsius deep freezer, or soaked in a methanol:chloroform mixture (1:1) at 4 degree Celsius.

(2) TOC Analysis of Sediment

Total carbon (TC) was extracted from 2 g of dried sediment with 100 mM sodium phosphate/5 mM EDTA buffer solution (pH 8.0), and TOC was calculated by finding the differences between the TC and the total inorganic carbon. The TC and TOC were measured by combustion oxidation infrared spectrophotometry in accordance with ISO8245 (See ISO8245: 1999, American National Standards Institute (2007), the contents of which are incorporated herein by reference).

(3) Glucose and Disaccharide Content of Hirondellea gigas

Five specimens of Hirondellea gigas were freeze-dried and then crushed. The crushed Hirondellea gigas was extracted three separate times with 1 ml of distilled water. After removing the insoluble particles by Centrifugation (15,000 rpm at 4 degrees Celsius for 10 minutes), the extract was centrifuged using a 10-KDa cut-off Microcon centrifugal filter device (Millipore Co., Billerica, Mass.) to remove enzymes and other high molecular weight components. The glucose content in the obtained supernatant was then measured using the Glucose CII kit (Wako Pure Chemical Industries, Ltd.). The maltose content was calculated from the increase in glucose levels after the reaction with 1 U of α-glucosidase (Oriental Yeast Co., Ltd.) took place at 37 degrees Celsius for 16 hours. The cellobiose content was also calculated from the increase in the glucose content after the reaction with 1 U of β-glucosidase (Oriental Yeast Co., Ltd.) took place at 37 degrees Celsius for 16 hours.

(4) Hydrolytic Enzyme Activity in Hirondellea gigas Extract

The enzymes from the crushed Hirondellea gigas were extracted three times with 0.5 ml of distilled water. All of the enzyme activities were measured at 30 degrees Celsius. The protease activity was measured by a modified Anson assay in which one unit of activity was defined as an amount of extract required to hydrolyze Hammerstein casein to produce a color equivalent to that of 1 μmole of tyrosine in a minute at pH 5.6 (See M. L. Anson, J. Gen. Physiol. 22, 79-89 (1938), the contents of which are incorporated herein by reference).

The amylase activity was detected by using iodine after incubating the Hirondellea gigas extract with 1% (w/v) soluble starch at pH 5.6. One unit of activity was defined as an amount of extract that hydrolyzed soluble starch to cause a 1% decrease in the absorbance at 620 nm in a minute.

The cellulase activity was measured with a cellulase assay kit (Megazyme) with 1% (w/v) AZO-CM-Cellulose. One unit was defined in accordance with the protocol of the manufacturer. During purification of HGcel, the cellulase activity of the Hirondellea gigas extract was measured as an amount of glucose produced from CMC. One unit of cellulase activity was defined as an amount that hydrolyzed CMC to produce 1 μg of glucose in a minute.

The mannanase activity was measured as an amount of reducing sugar detected by dinitrosalicylic acid (DNS) assay after the reaction with 0.2% (w/v) glucomannan at pH 5.6 (See M. G. Lorenz, Anal. Chem. 31, 426-428 (1959), the contents of which are incorporated herein by reference). One unit was defined as an amount of Hirondellea gigas extract that was required to hydrolyze glucomannan to produce 1μ mole of reducing sugar in a minute.

The xylanase activity was measured with an endo-β-xylanase assay kit (Megazyme). One unit was calculated from the activity of xylanase (*Trichoderma longibrachiatum*) that was used as a control, which was included in the kit.

The α-glucosidase activity was measured as an amount of glucose produced at pH 5.6 with 1% (w/v) maltose being used as substrate. One unit was defined as an amount that decomposed maltose to produce 1μ mole of glucose in a minute at pH 5.6.

All of the enzyme activities were calculated based on the protein content of the sample solution. The protein content was measured by Bradford assay using bovine serum albumin as a standard material (See M. M. Bradford, Anal. Biochem. 72, 248-254 (1976), the entire contents of which are incorporated herein by reference).

(5) TLC Analysis of Oligosaccharides

Soluble starch (1.0% (w/v)) and the Hirondellea gigas extract were added to a 50 mM sodium acetate buffer solution (pH 5.6), and were incubated at 40 degrees Celsius. Samples were taken at intervals and boiled for 5 minutes. The product was analyzed using TLC with the use of a butanol/acetic acid/water (2:1:1 (v/v/v)) solvent. "S" represents maltooligosaccharides or cellooligosaccharides (FIG. 2).

(6) Test in which Sawdust was Used as Substrate

Sawdust of live oak, which was purchased from Adachi Sawmill, was washed twice with water, autoclaved at 121 degrees Celsius for 15 minutes, washed twice with DDW, and then dried in air at room temperatures. The dried sawdust was suspended in a sodium acetate buffer solution (pH 5.6) at a concentration of 5% (w/v), and then incubated with enzyme preparations at 35 degrees Celsius. The digestion rate of the sawdust was calculated by measuring the concentrations of glucose and cellobiose in the aqueous phase of the reaction mixture. Incidentally, even when either carboxymethylcellulose or sawdust was used as substrate, the same amounts of enzymes were used in experiments.

(7) Purification of HGcel

Ten individuals of Hirondellea gigas, which were put into a 50 ml tube without being crushed, were added to 20 ml of DDW that contained 200 μL of a protease inhibitor cocktail (Nacalai Tesque), and were incubated with gentle shaking at 4 degrees Celsius for 14 hours.

Ten individuals of Hirondellea gigas were put into a 50 ml tube, and 20 ml of sterile distilled water containing 200 μl of a protease inhibitor mixed solution were added, and were shaken at 4 degrees Celsius for 14 hours. The supernatant was obtained after centrifugation (1000×g for 10 minutes at 4 degrees Celsius). To the residue of Hirondellea gigas, 10 ml of sterile distilled water containing 100 μl of a protease inhibitor mixed solution were added again, and were stirred on ice, and the supernatant was obtained after centrifugation (1000×g for 10 minutes at 4 degrees Celsius). This operation was repeated twice, and the obtained supernatants were put together, and a supernatant mixed solution was obtained as a result.

Saturated ammonium sulfate was added to the obtained supernatant mixed solution in such a way that the final concentration thereof came to 30% (w/v). After the extract was incubated on ice for 30 minutes, the extract was subjected to centrifugation (8,000×g for 30 minutes at 4 degrees Celsius), the supernatant was collected and adjusted to a concentration of 60% ammonium sulfate, and the sample was incubated on ice for 3 minutes. The precipitate demonstrating cellulase activity was collected by centrifugation (8,000×g for 30 minutes at 4 degrees Celsius), and suspended in 2 ml of DDW. A 2-ml aliquot was desalted and then concentrated to 50 μl with the use of Amicon Ultra 50K (Millipore Co.). Then, 50 μL of enzyme concentrate was applied to a 1 ml hi-trap Mono-Q sepharose anion exchange column (Tosoh Corporation), which was equilibrated with the use of a 20 mM sodium phosphate buffer solution (pH 6.8) (Amersham Pharmacia Biotech, Inc.), and then was sequentially eluted by 3 ml of a 20 mM sodium phosphate buffer solution (pH 6.8) containing 0.1M increments of NaCl so that the final salt concentration came to 0.6M.

Figure 3A:
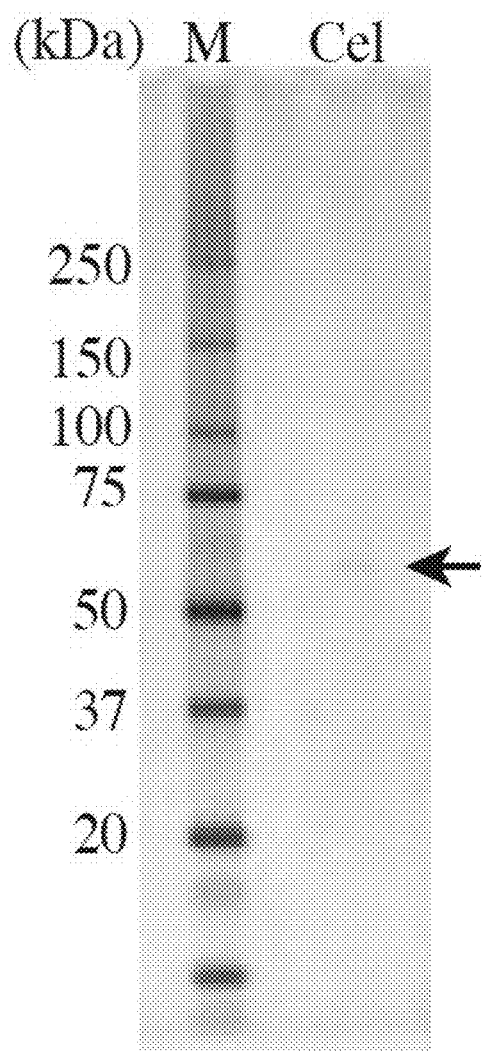
FIG. 3a is a diagram demonstrating that HGcel, which was obtained from extract of crushed Hirondellea gigas through purification with the use of anion exchange column chromatography as described later in examples, was identified as a single 59 kDa band on SDS-PAGE (5 to 20% gradient gel).

The cellulase activity was detected in a 0.5M-NaCl fraction. The fraction was diluted with DDW and concentrated to 50 μL with the use of Amicon Ultra 50K. The concentrate was applied to the abovementioned equilibrated column, and eluted as described above but to a final salt concentration of 0.5M. The fractions containing cellulase were collected, washed with DDW, concentrated to 50 μL with the use of Amicon Ultra 50K, and then transferred onto a DEAE-Toyopearl anion exchange column (10 mM Tris-HCl (pH 8.6)). The elution from the column was sequentially carried out with 0 to 0.6M NaCl by 0.2M. The cellulase activity was measured based on the amounts of glucose produced after a reaction with 1% (w/v) CMC (pH 5.6). The purity and molecular weight of the final enzyme preparation were assessed by SDS polyacrylamide gel electrophoresis (FIG. 3a).

(8) DNA Extraction, PCR Amplification, and Sequencing

The amphipods (Hirondellea gigas) were immersed in chloroform upon collection. DNA was extracted from 1 g of these amphipods with the use of DNEasy Blood & Tissue Kit (Qiagen) according to the manufacturer's instructions. The 16S rDNA of bacteria and archaea was subjected to PCR by using: universal primer pair "Bac27f (5'-AGAGTTTGATC-CTGGCTCAG-3') (SEQ ID NO: 1)" and "Bac1492r (5'-GGTTACCTTGTTACGACTT-3') (SEQ ID NO: 2)", or "Arch21F (5'-TTCCGGTTGATCCYGCCGGA-3') (SEQ ID NO: 3)" and "Arch958R (5'-YCCGGCGTTGAMTC-CAATT-3') (SEQ ID NO: 4)". PCR amplification (in a 25 μl reaction system) was carried out by using SpeedStar-HS DNA polymerase (Takara Bio Inc.), GeneAmp PCR System 9700 (Applied Biosystems) and the buffer solution supplied with the enzymes.

The PCR conditions were as follows: an initial incubation at 96 degrees Celsius for 30 seconds; 30 cycles at 5-second interval at 98 degrees Celsius; an incubation at 55 degrees Celsius for 10 seconds; an incubation at 72 degrees Celsius for 15 seconds; followed by a final extension step at 72 degrees Celsius for 2 minutes.

The PCR products were analyzed by electrophoresis on a 1% agarose gel purified with the use of Exo-SAP digestion with Exonuclease I (USB Corp.) and shrimp alkaline phosphatase (SAP, Promega KK) at 37 degrees Celsius for 20 minutes, and then treated at 80 degrees Celsius for 30 minutes to inactivate the enzymes. The PCR products were sequenced using the primers described above and the DYEnamic ET Dye Terminator reagent (GE Healthcare Life Sciences) on a MegaBACE 1000 (Amersham Biosciences) automatic sequencer. The nucleotide sequences were trimmed, assembled, and translated using Sequencher 3.7 software (Gene Codes Corp.).

(9) Amino-Acid Sequencing Analysis of Purified HGcel

HGcel derived from 10 individuals of the amphipod (Hirondellea gigas) was partially purified (60% ammonium sulfate precipitation followed by DEAE Toyopearl anion exchange chromatography as described above). The cellulase-containing fractions were collected, pooled, desalted, and then concentrated. The cellulase preparation was subjected to SDS-PAGE, and visualized by staining with Coomassie Brilliant Blue R-250 (Sigma-Aldrich Co.). A single 59-kDa band observed was excised from the gel, and digested with trypsin. After this treatment, the peptides were analyzed using LC-MS/MS system (HPLC: Paradigm MS2, Michrom Bioresources, Inc.; MS: Q-Tof2, Waters Micromass). All of the MS data (mass spectrometry) were analyzed using the Mascot Server (Matrix Science Ltd.).

(10) Production of Glucose from Copy Paper by Purified HGCel

A 3.8 mg piece of copy paper was immersed in an enzyme preparation solution containing 0.28 U of HGCel. Then, the piece of copy paper was air-dried. After the reaction took place at a room temperature (25 degrees Celsius) for 15 hours, and the amount of glucose produced was measured by Glucose CII kit reagent (Wako Pure Chemical Industries, Ltd.).

2. Results (1) Capturing of Hirondellea gigas

In order to observe how Hirondellea gigas thrives at the greatest ocean depth, a 10,000 m-class free-fall sediment sampler with a camera system "ASHURA" was sent down into the Challenger Deep to observe Hirondellea gigas. Moreover, baited traps were used to capture Hirondellea gigas (11°22.11'N, 142°25.86'E, Depth: 10,897 m). As a result, the inventors succeeded in capturing 185 individuals in 3 hours.

Figure 1B:
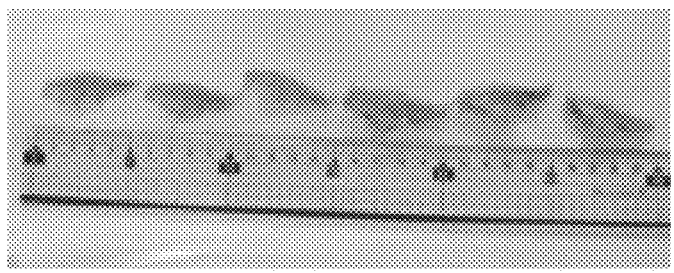
FIG. 1b is a diagram proving that all the individuals in the baited trap shown in FIG. 1a were in the same form, and showing that they were the amphipods which were about 3 to 5 cm in length.

Hirondellea gigas was the only organism that was captured (See FIG. 1a). The individuals captured ranged from 2 cm to 5 cm in length, and 0.3 g to 0.6 g in dry weight (See FIG. 1b)

(2) Hydrolytic Enzymes in Bodies of Hirondellea gigas

Figure 1C:
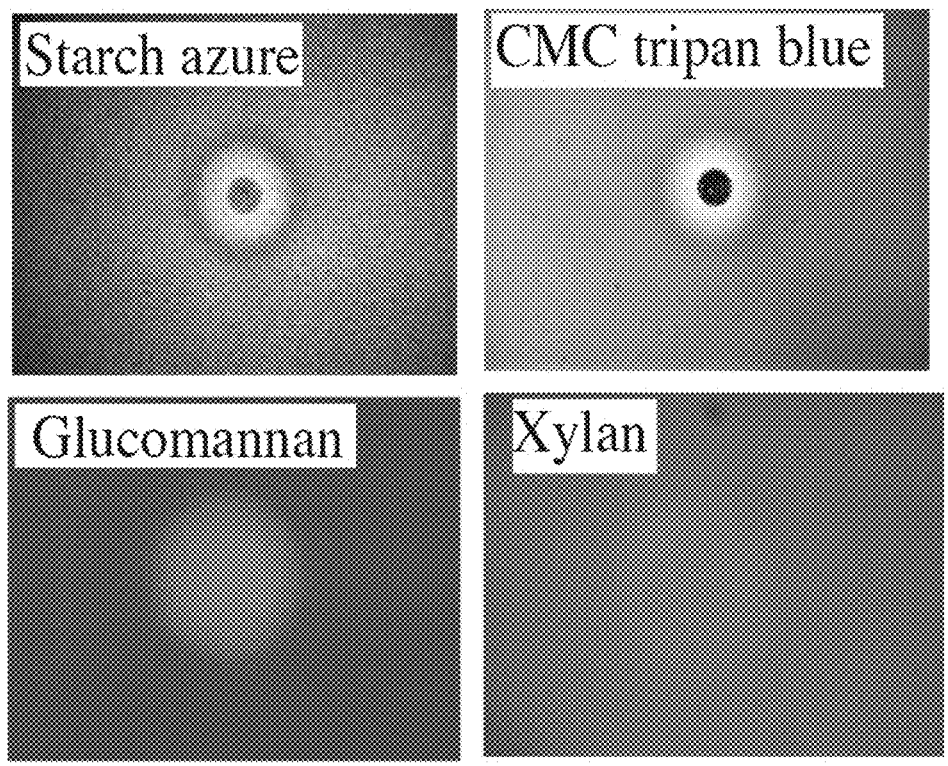
FIG. 1c is a diagram showing the activity of degrading enzymes, which were evaluated by halo formation in agar plates containing starch azure (amylase), CMC trypan blue (cellulase), glucomannan (mannanase), and xylan (xylanase); the halos generated by the amylase activity and the cellulase activity were directly visible, but the halos showing the mannanase activity and the xylanase activity were detected after being stained with 0.5% Congo Red and then washed with deionized distilled water (DDW).

The hydrolytic enzymes synthesized by Hirondellea gigas were confirmed by using the extract obtained by crushing Hirondellea gigas and observing halos formed on agar plates that contained each substrate. Halos were confirmed on the agar plates containing, as substrates, starch, carboxymethyl cellulose (CMC), glucomannan, and xylan (See FIG. 1c). The activities of amylase, cellulase, mannanase, xylanase, α-glucosidase, and protease were measured by using five individuals of Hirondellea gigas that were randomly selected (See Table 1).

TABLE 1

| Sample ID | amylase (mU) | cellulase (mU) | mannanase (μU) | xylanase (μU) | α-glucosidase (μU) | protease (mU) |
|---|---|---|---|---|---|---|
| 1 | 112.2 | 3.42 | 8.16 | 0.41 | 22.2 | 0.26 |
| 2 | 94.3 | 2.40 | 16.1 | 0.37 | 17.1 | 0.27 |
| 3 | 65.5 | 2.26 | 39.8 | 0.36 | 15.3 | 0.17 |
| 4 | 65.4 | 2.25 | 30.2 | 0.43 | 13.7 | 0.17 |
| 5 | 93.8 | 3.22 | 16.6 | 0.40 | 27.6 | 0.23 |

(per microgram of protein)

As a difference between the individuals, it was confirmed that there was a difference in the activity in the range of 1.5 to 5 times. Those kinds of polysaccharide hydrolase are considered to be available for assimilating wood-derived cellulose and hemicellulose (See B. Goodell, et al., J. Biotechnol., 53, 133-162 (1997), the contents of which are incorporated herein by reference). While the above enzymes were detected, the regnase activity was not detected. Furthermore, the enzyme activities of bait used in the traps were not detected.

(3) Reaction Products of Hydrolytic Enzymes

Figure 1D:
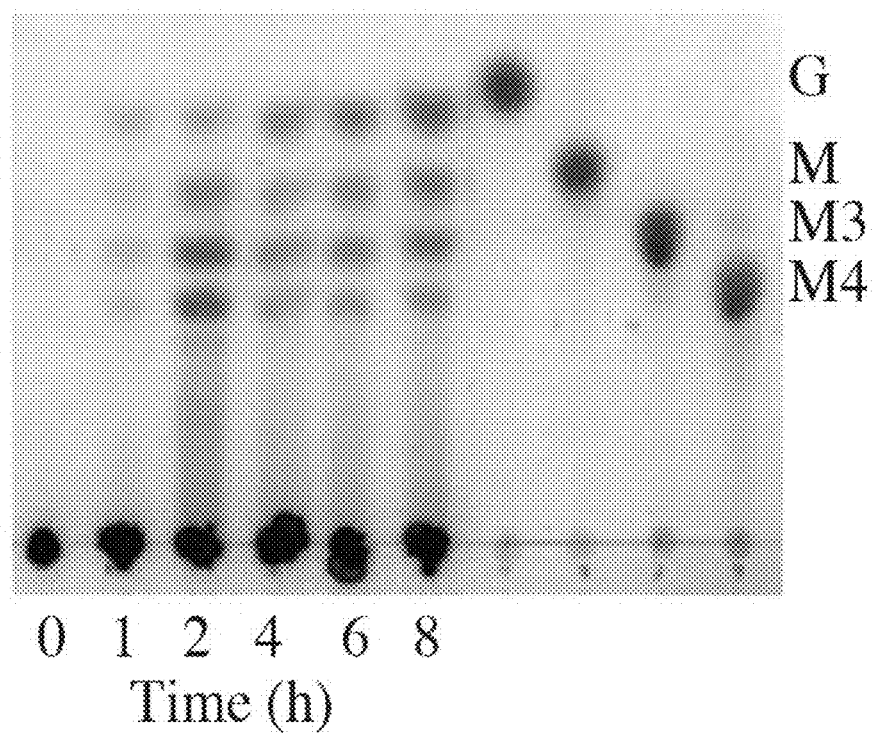
FIG. 1d is a diagram showing reaction speed determined by TLC; protein extract obtained from crushed Hirondellea gigas was reacted with 0.5% (w/v) starch at 30 degrees Celsius in a 100 mM sodium acetate buffer solution (pH 5.6).
Figure 1E:
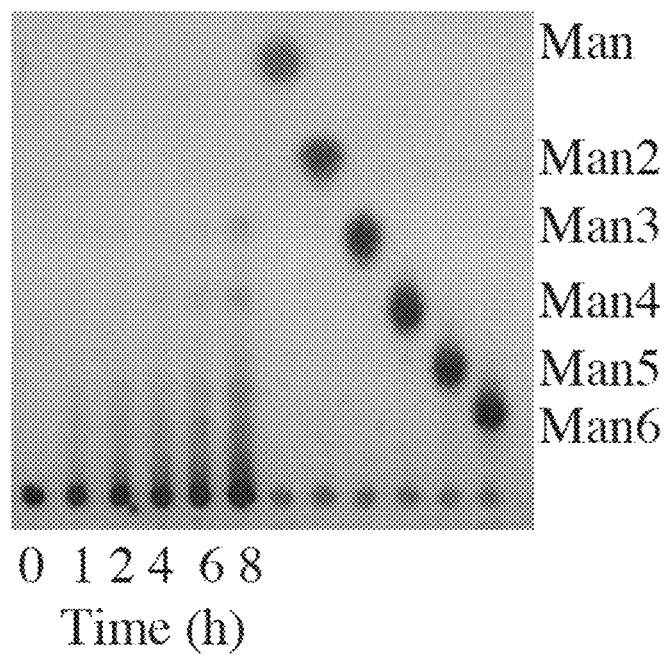
FIG. 1e is a diagram showing reaction speed determined by TLC; protein extract obtained from crushed Hirondellea gigas was reacted with 0.2% (w/v) glucomannan at 30 degrees Celsius in a 100 mM sodium acetate buffer solution (pH 5.6).
Figure 1F:
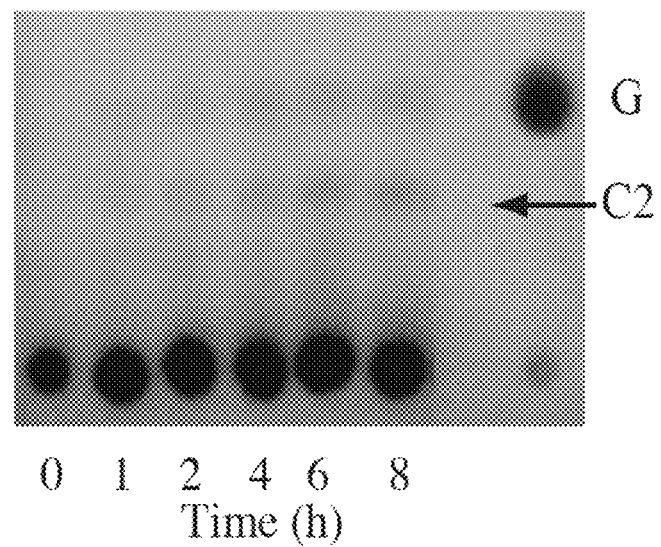
FIG. 1f is a diagram showing reaction speed determined by TLC; protein extract obtained from crushed Hirondellea gigas was reacted with 1% (w/v) CMC at 30 degrees Celsius in a 100 mM sodium acetate buffer solution (pH 5.6).

The 80% saturated ammonium sulfate precipitations of the crushed Hirondellea gigas were used as crude enzymes. Thin-layer chromatography (TLC) was used to measure substrate decomposition products. With the help of the amylase activity in the crude enzymes, glucose, maltose, maltotriose, and maltotetraose were produced from potato starch at 30 degrees Celsius (See FIG. 1d). With the help of the mannanase activity in the crude enzymes, glucomannan was decomposed, and many low-molecular-weight polysaccharides were produced. The digestion pattern of glucomannan represented typical characteristics of endo-type polysaccharide hydrolase (See FIG. 1e). Galactomannan and curdlan could be not detected.

(4) Optimum pH of Hirondellea gigas Extract as Crude Enzymes

Figure 1G:
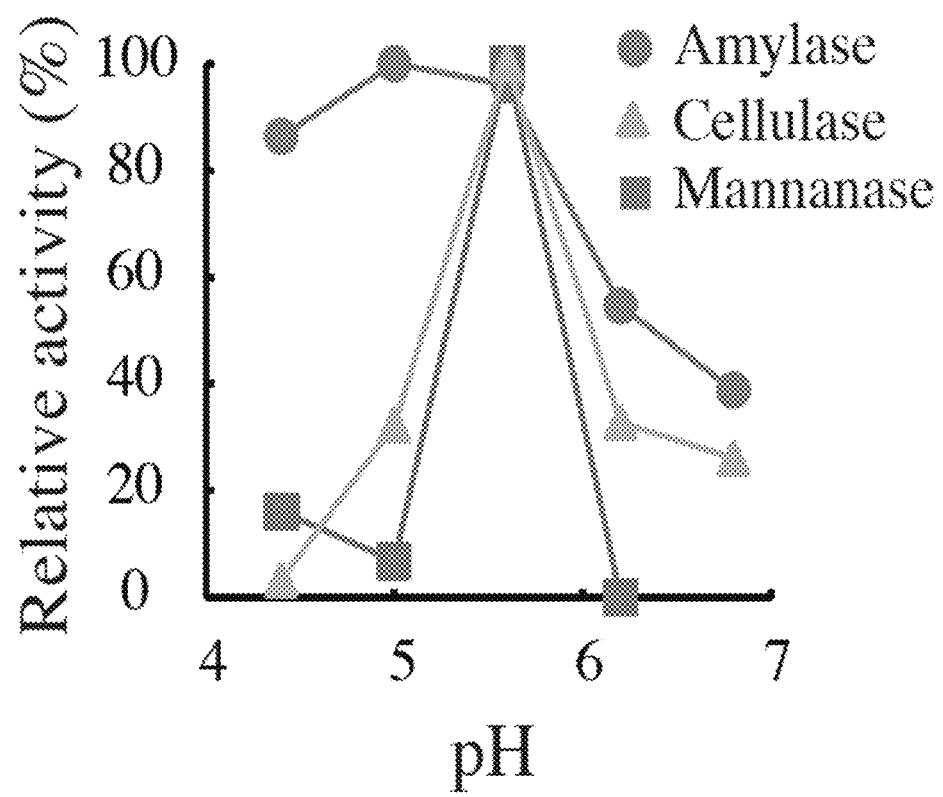
FIG. 1g is a diagram showing each pH dependence of amylase activity, mannanase activity, and cellulase activity determined with the use of protein extract obtained from crushed Hirondellea gigas; the enzymatic reaction took place in a 100 mM sodium acetate buffer solution (pH 4.4 to 5.6) or a 100 mM sodium phosphate buffer solution (pH 6.2 to 6.8) at 30 degrees Celsius; the diagram shows relative activity against the base value of pH 5.6 where the activity was highest.

The catalytic activity of the Hirondellea gigas extract had a peak between pH 5.2 and pH 6.0; at pH 8.0, the activity went away (See FIG. 1g). Given the fact that the pH is 8.0 in the Challenger Deep, the above results suggest that those kinds of polysaccharide hydrolase are active in the bodies of Hirondellea gigas. Furthermore, the ability of the enzyme activity to hydrolyze wood into cellulose and hemicellulose strongly raises the possibility that Hirondellea gigas is able to extract nutrients from wood in the deepest part of the deep.

(5) Oligosaccharide Composition in Bodies of Hirondellea gigas

Figure 2A:
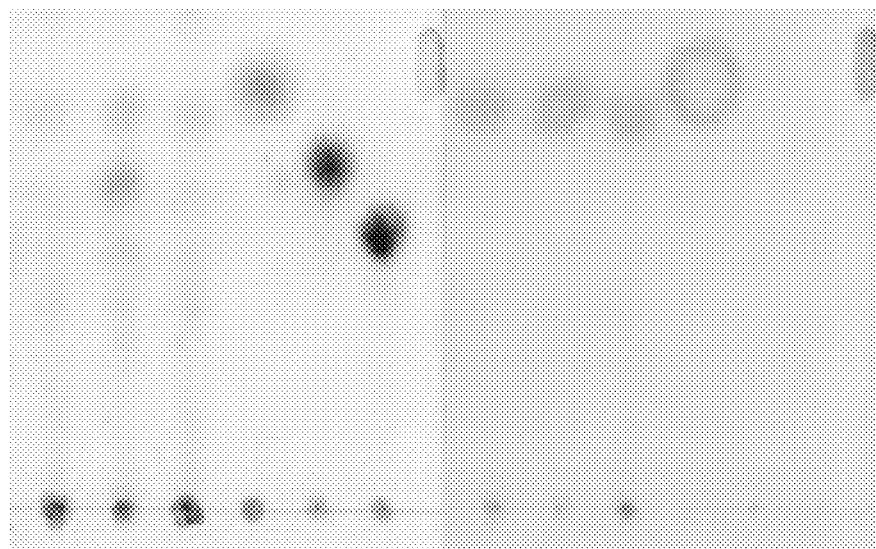
FIG. 2a is a diagram showing results of identifying oligosaccharides, which exist in extract obtained from the entire crushed Hirondellea gigas; oligosaccharides were extracted by DDW from three individuals of crushed Hirondellea gigas, and were separated on TLC; the oligosaccharides were then stained with sulfuric acid (Left), or glucose was stained by Glucose CII kit (Wako Pure Chemical Industries, Ltd.) (Right).
Figure 2B:
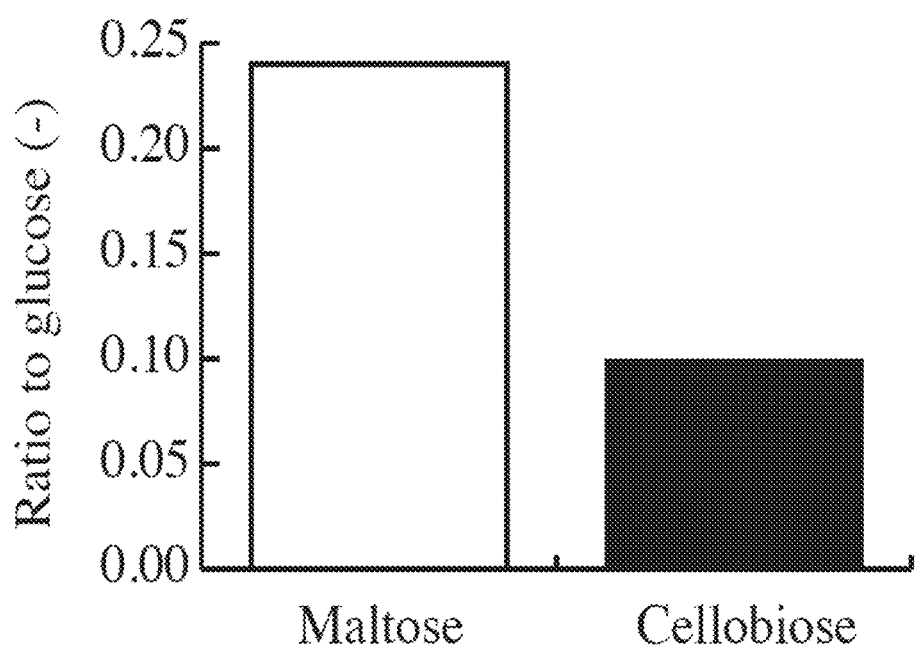
FIG. 2b is a diagram showing results of identifying oligosaccharides, which exist in extract obtained from the entire crushed Hirondellea gigas; the maltose or cellobiose content was measured based on an increased glucose content after the extract was treated with α- or β-glucosidase.

In order to verify the above hypothesis, the composition of oligosaccharides in the bodies of Hirondellea gigas was measured. It was proved that two individuals of Hirondellea gigas contained glucose and disaccharides, and that there was a polysaccharide hydrolase activity in the bodies (FIG. 2a). The average amount of glucose contained was 0.43±0.1% (w/w) (dry mass) (n=5). The amounts of disaccharides contained were significantly different between the individuals. By using 30 individuals of Hirondellea gigas, the composition of disaccharides in the bodies was measured: the amounts of maltose and cellobiose contained were 35% and 17%, respectively, of the amount of glucose contained (See FIG. 2b).

Figure 3B:
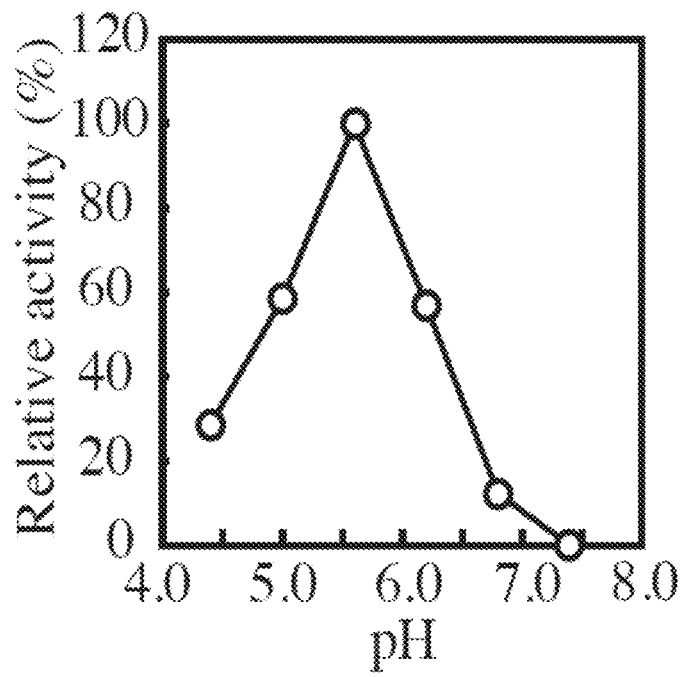
FIG. 3b is a diagram showing the relationship between enzyme activity and pH of HGcel, and showing relative activity against the base value of pH 5.6 where the activity was highest; as for the enzyme activity, 1% (w/v) carboxymethylcellulose was used as substrate, and the reaction took place at 30 degrees Celsius for 20 minutes, and the produced glucose was then determined by Glucose CII kit; relative values at each pH were calculated with the amount of glucose produced at pH 5.6 as 100%.
Figure 3C:
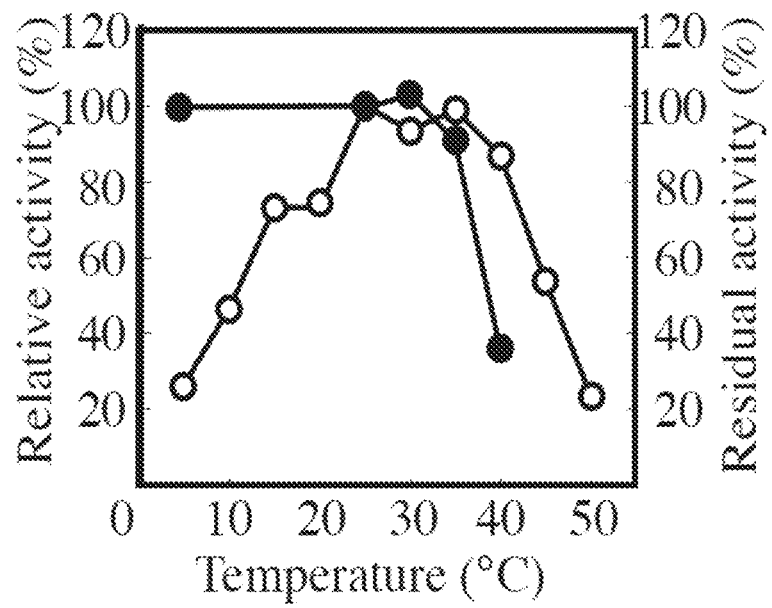
FIG. 3c is a diagram showing the relationship between enzyme activity and temperature of HGcel, and showing relative activity (○) and remaining activity (●) against the base value at 30 degrees Celsius where the activity was highest; as for the enzyme activity, 1% (w/v) carboxymethylcellulose was used as substrate, and the reaction took place in a 100 mM sodium acetate buffer solution (pH 5.6) at each temperature for 20 minutes, and the produced glucose was then measured by Glucose CII kit; relative values at each reaction temperature were calculated with the amount of glucose produced at 30 degrees Celsius as 100%; the diagram shows that the optimum temperature, which indicates a maximum value of enzyme activity, is 25 to 35 degrees Celsius, and that the temperature where temperature stability is confirmed is 5 to 35 degrees Celsius where the remaining activity is 80% or more.
Figure 5:
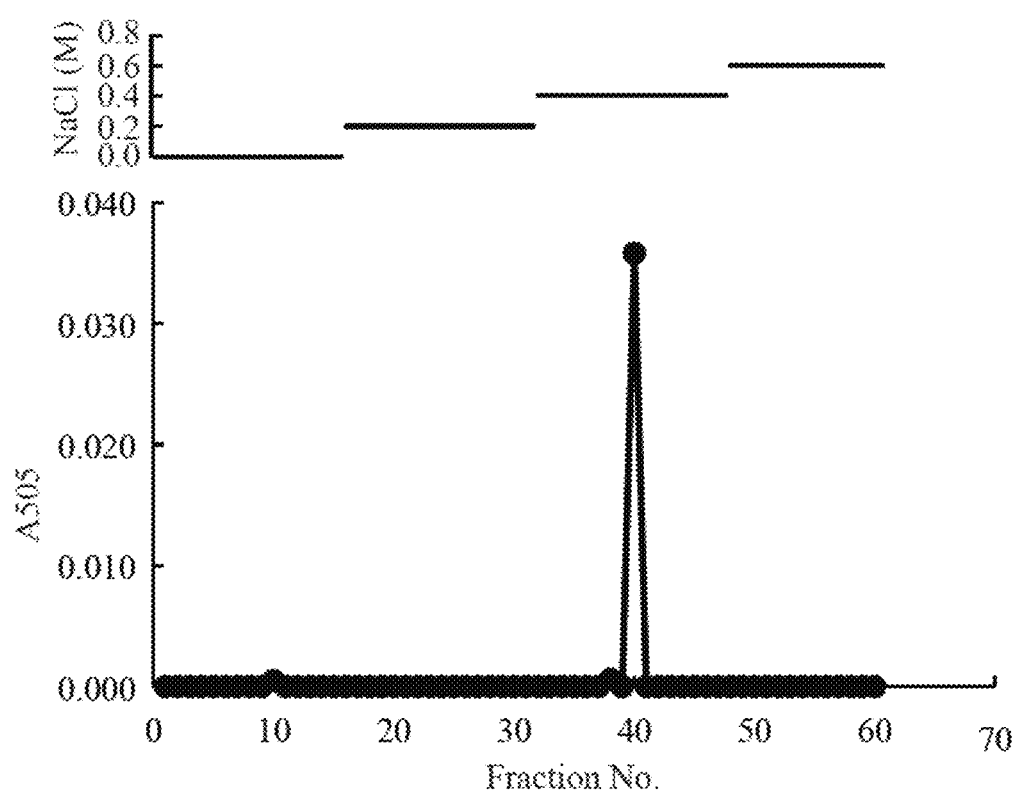
FIG. 5 is a diagram showing a final step of HGcel purification with the use of DEAE-Toyopearl; HGcel was eluted from 0.5 mL of DEAE-Toyopearl that was equilibrated with a 10 mM tris-hydrochloric acid buffer solution (pH 8.6); with the use of 0 to 0.6M of sodium chloride, HGcel was sequentially eluted per 0.2M thereof; the volume of each elution buffer was 1.5 ml; the fraction amount was about 0.1 ml; the cellulase activity was determined as glucose concentration as described later in examples; the 40th fraction contained cellulase activity, which was confirmed as only one band on SDS-PAGE (See FIG. 3a).

(6) Properties of HGcel, a Purified Enzyme Derived from Hirondellea gigas Extract Novel cellulase, HGcel, was obtained and purified from 10 individuals of Hirondellea gigas. SDS-PAGE determined that the molecular weight of HGcel was 59 kDa (See FIGS. 3a and 5). The optimum pH of the cellulase activity for hydrolyzing cellulose was 5.6 (See FIG. 3b). The cellulase activity was not detected at pH 7.8 (which was the same level of pH as in the seabed). At pH 5.6, the optimum temperature was 25 to 35 degrees Celsius (FIG. 3c). Surprisingly, the enzyme kept 20% or more of its activity even at 4 degrees Celsius, and the activity was most stable at 35 degrees Celsius. Furthermore, the activity began fading away as the temperature rose above 40 degrees Celsius (See FIG. 3c).

Since the N-terminus of the enzyme was blocked, the internal amino-acid sequence of HGcel was determined by mass spectrometry with the use of tryptic peptides. It was confirmed that amino-acid sequences of three types of peptides, P1, P2, and P3, were TPPMGWLAWER (SEQ ID NO: 5), SQMALWAIMAAPLFMSNDL (SEQ ID NO: 6), and AVIAVNQDPLGIQGR (SEQ ID NO: 7), respectively. The sequences of P1 and P2 were identical to those of various types of α-N-acetylgalactosaminidase [which were respectively rhesus macaque (Macaca mulatta) (Accession No. XP_001117342), α-N-acetylgalactosaminidase-like protein (Accession No. XP_001117342) of Nile tilapia (Oreochromis niloticus), and GHF31 (Accession No. XP_002059881.1) of Drosophila virilis (Drosophila virilis) (See A. G. Clark, et al., Nature. 450, 203-218 (2007), the contents of which are incorporated herein by reference)]. Alignment was carried out between the sequence of P3 and the sequence of α-N-acetylgalactosaminidase. It was found that there was a deletion or mismatch of one or two between the sequences (See Z. Fujimoto, et al., J Biol Chem, 278, 20313-20318 (2003), the contents of which are incorporated herein by reference).

Figure 3D:
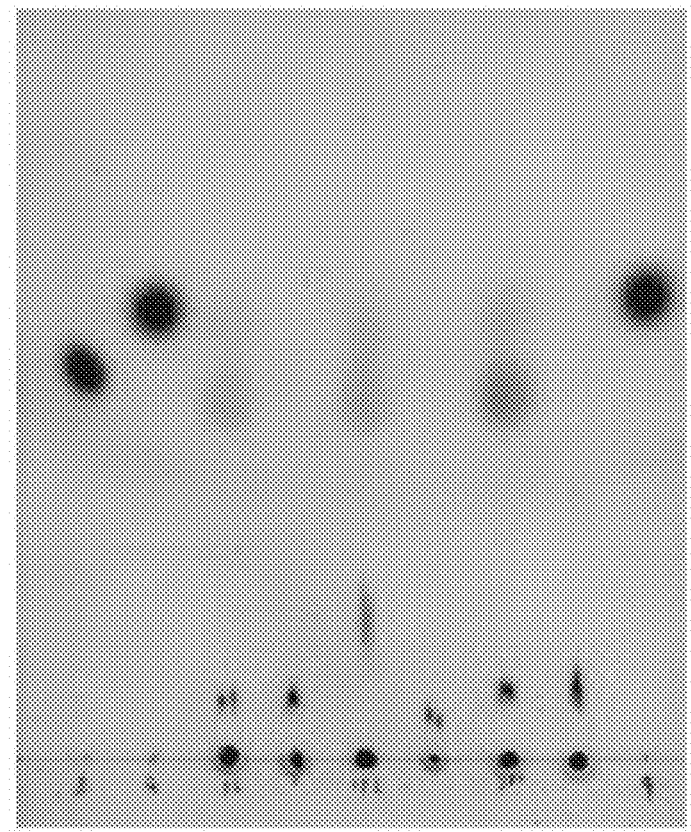
FIG. 3d is a diagram demonstrating that HGcel converted carboxymethylcellulose into glucose (Glu) and cellobiose (C2); the diagram shows the amounts of glucose and cellobiose contained after 200 mU of HGcel was added to 500 μL of a 5% (w/v) cellulose solution (pH 5.6) and reacted at 30 degrees Celsius for 96, 192, and 288 hours (+E); control was the amounts determined in the similar manner without adding HGcel (R).
Figure 3E:
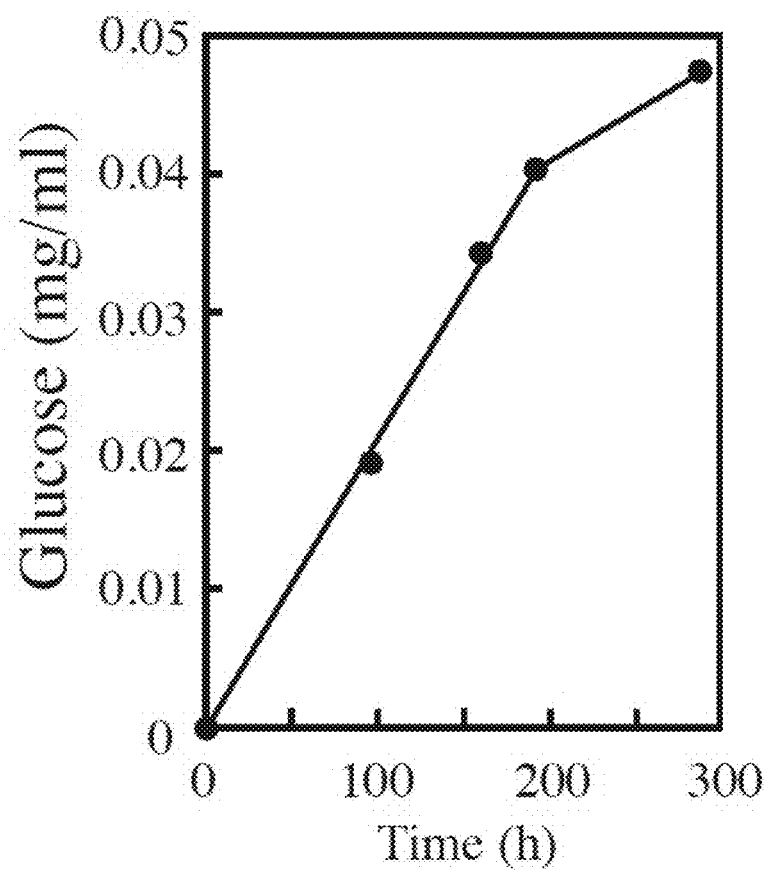
FIG. 3e is a diagram showing the reaction speed of the glucose production from cellulose by the use of HGcel.
Figure 3F:
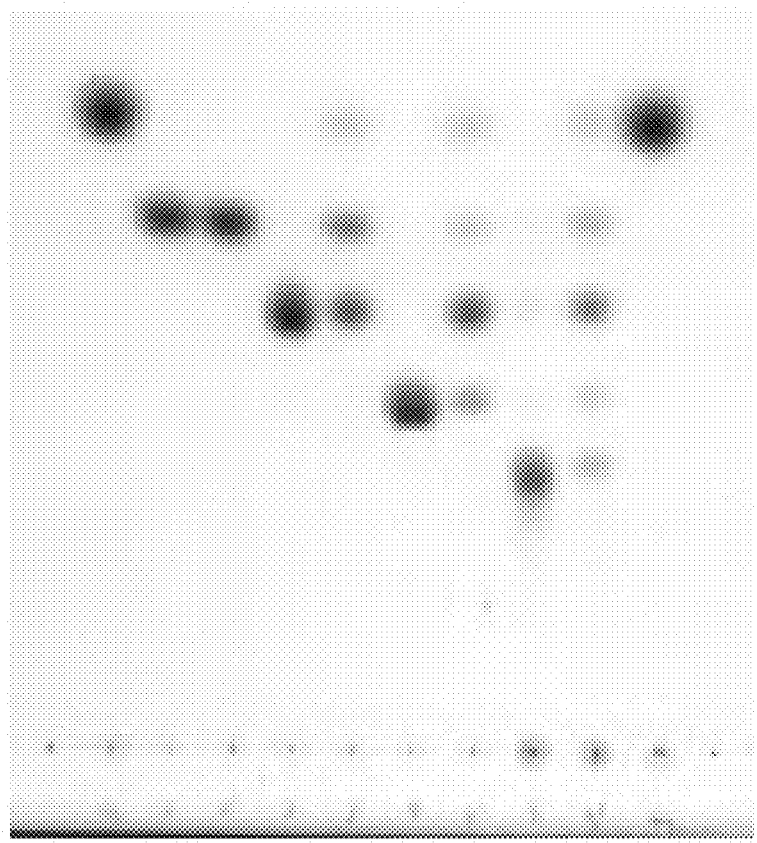
FIG. 3f is a diagram showing results of TLC analysis of products obtained after a reaction of HGcel with cellobiose (C2), cellotriose (C3), cellotetraose (C4), and cellopentaose (C5) as substrates; the system in which the reaction took place with HGcel (12 mU) is represented by "+", and the system in which HGcel was not added is represented by "−" as a control; the diagram shows that HGcel has the activity to hydrolyze cello oligosaccharides, or those beyond cellotriose.

HGcel produced glucose and cellobiose in a molar ratio of 2:1 from CMC. Moreover, HGcel produced glucose and cellobiose by decomposing crystalline cellulose (See FIGS. 3d and 3e). Furthermore, HGcel produced glucose by decomposing cello-oligomers, which were larger than cellotriose (See FIG. 3f).

Figure 3G:
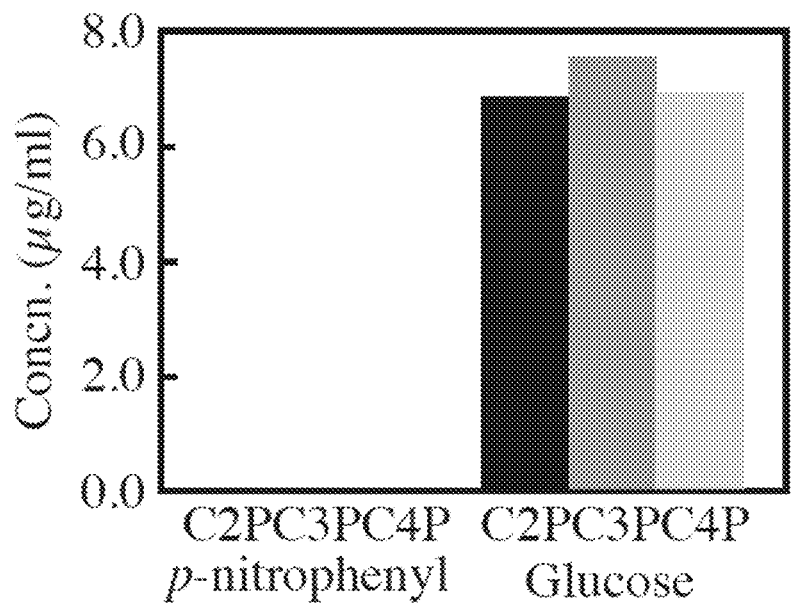
FIG. 3g is a diagram showing the amounts of free glucose or free p-nitrophenol (μg/mL) after HGcel (12 mU) was reacted at 35 degrees Celsius for one hour with p-nitrophenyl cello oligosaccharides and a p-nitrophenyl group was then linked to a reducing end of cello oligosaccharides.

HGcel produced glucose by hydrolyzing cellobiose, cellotriose, and cellotetraose, and coupled their reducing ends with p-nitrophenyl; the absorbance of p-nitrophenyl was not detected (See FIG. 3g).

Based on the above results, it was confirmed that HGcel is novel exo-type cellulase, and has the activity to produce glucose and cellobiose by hydrolyzing non-reducing ends of cellulose. The style of hydrolysis by HGcel is different from those of herbivorous animals or microorganisms, i.e. endo-β-glucanase (EC 3.2.1.4), cellobiohydrolase (EC 3.2.1.91), and β-glucosidase (EC 3.2.1.21) (See H. Watanabe et al., Nature. 394, 330-331 (1998) and H. Watanabe et al., Cell Mol. Life. Sci. 58, 1167-1178 (2001), the contents of which are incorporated herein by reference).

Figure 3H:
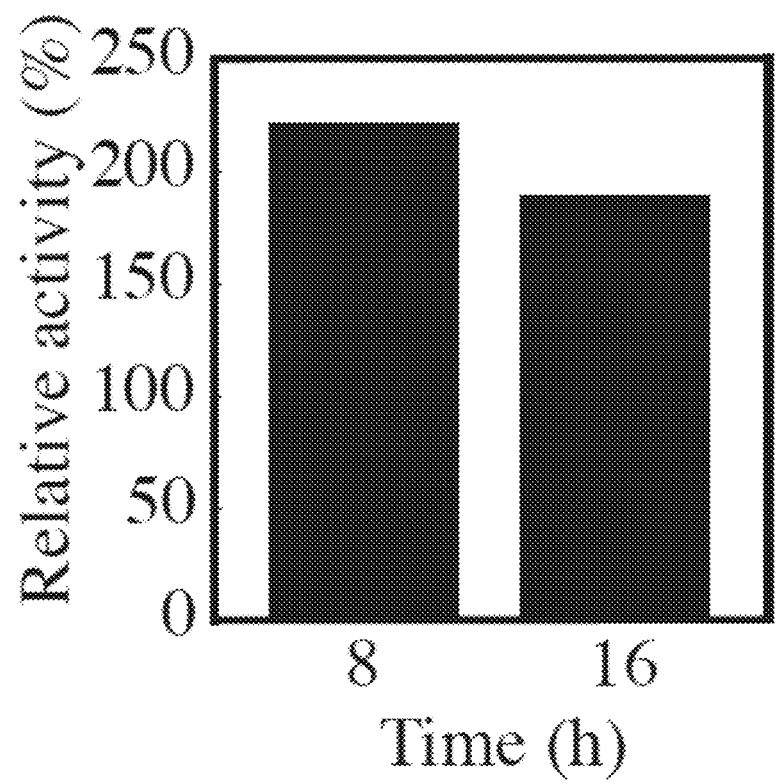
FIG. 3h is a diagram showing effects of hydrostatic pressure (100 MPa) on enzyme activity; the effects are shown as relative activity (%) against the base enzyme activity under atmospheric pressure (0.1 MPa); the enzymatic reaction took place in a 2-degree-Celsius airtight plastic tube with the use of 10 mU HGcel containing a 1% CMC solution; the enzyme activity was measured 8 or 16 hours after incubation.
Figure 3I:
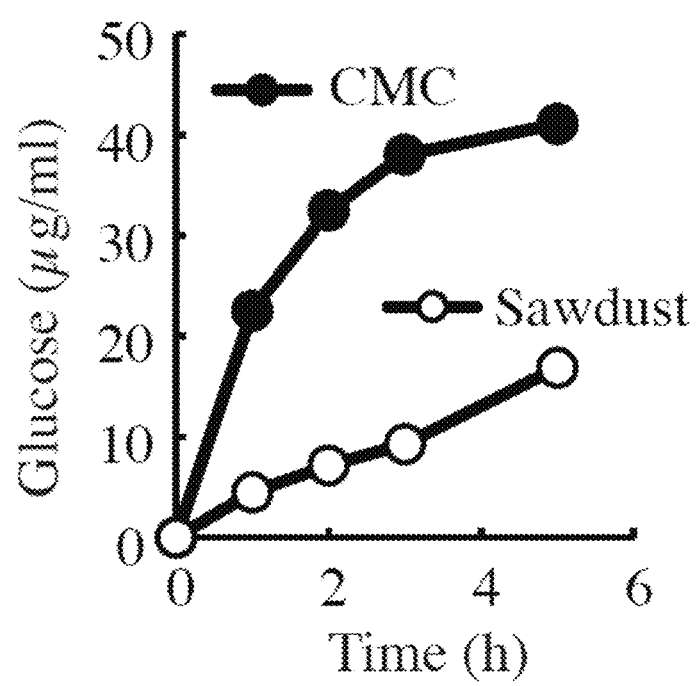
FIG. 3i is a diagram showing the reaction speed according to decomposition of CMC and sawdust by the use of HGcel, which were measured by determining the glucose content; HGcel (380 mU) was reacted with CMC or sawdust at 35 degrees Celsius.

The enzyme activity of HGcel enhanced under a condition of high hydrostatic pressure (100 MPa at 2 degrees Celsius) that was close to the habitat of Hirondellea gigas (See FIG. 3h). Moreover, HGcel decomposed not only CMC that was non-crystalline cellulose, but also sawdust that was crystalline cellulose, into glucose at 35 degrees Celsius (See FIG. 3i). The molar ratio of glucose and cellobiose produced by HGcel in the case of employing sawdust as a substrate was 2:1, which was the same ratio as the case of employing CMC as a substrate. However, the amount of glucose produced from sawdust was about one-fifth of the amount produced from CMC.

Figure 6:
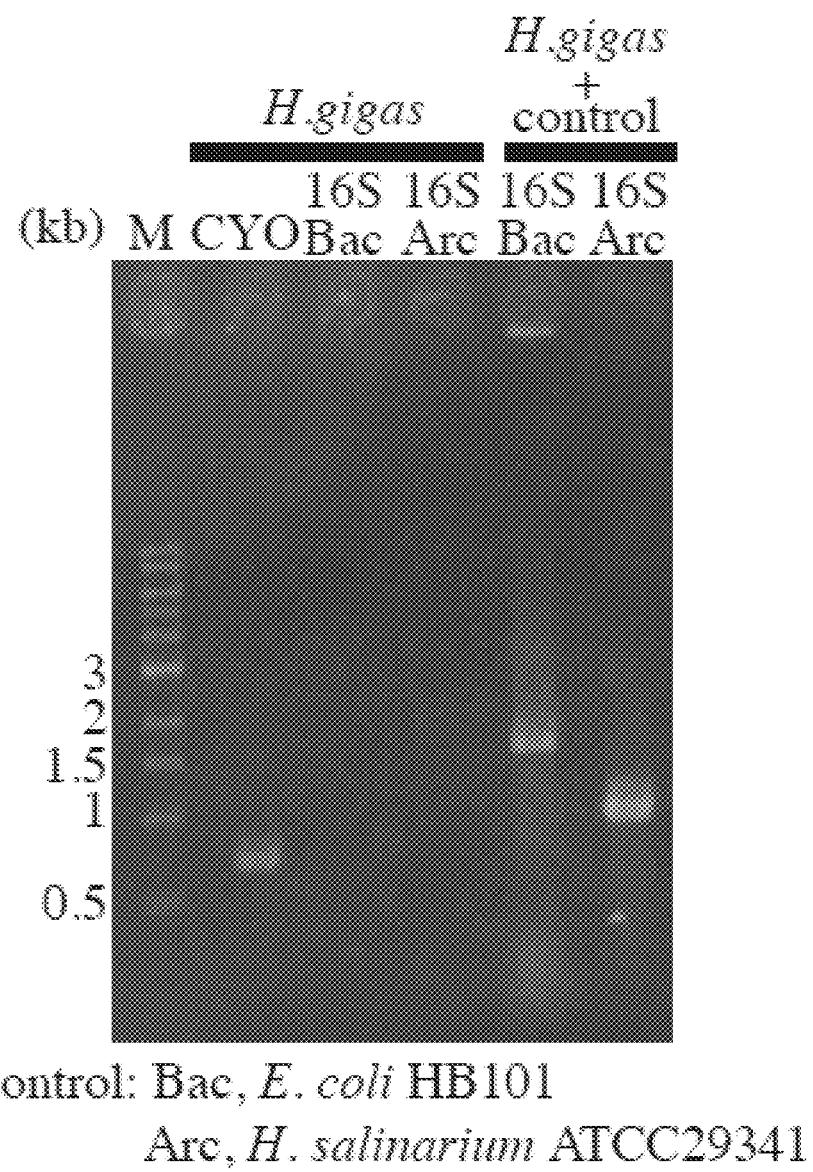
FIG. 6 is a diagram showing results of PCR analysis for 16S ribosomal DNAs of bacteria (Bac) or archaea (Arc) in Hirondellea gigas; as a positive control, cytochrome oxidase subunit I (CYO) DNA of mitochondria was subjected to PCR reaction; as positive controls for bacteria and archaea, DNAs of E. coli HB101 and halobacterium salinarium (Halobacterium salinarium) ATCC29341 were respectively used; "M" in the diagram represents a DNA marker.

By using PCR, attempts were attempted to detect rDNAs of bacteria, archaea, or eukaryotes from Hirondellea gigas. However, no clear PCR signals could be detected, and microorganisms could not be isolated from Hirondellea gigas (See FIG. 6). This leads to the conclusion that HGcel was an endogenous product of Hirondellea gigas. The higher hydrostatic pressure of the hadal zone is presumed to pose an obstacle to the lives of other organisms.

(7) Production of Glucose by HGcel from Copy Paper and Sawdust

Figure 7A:
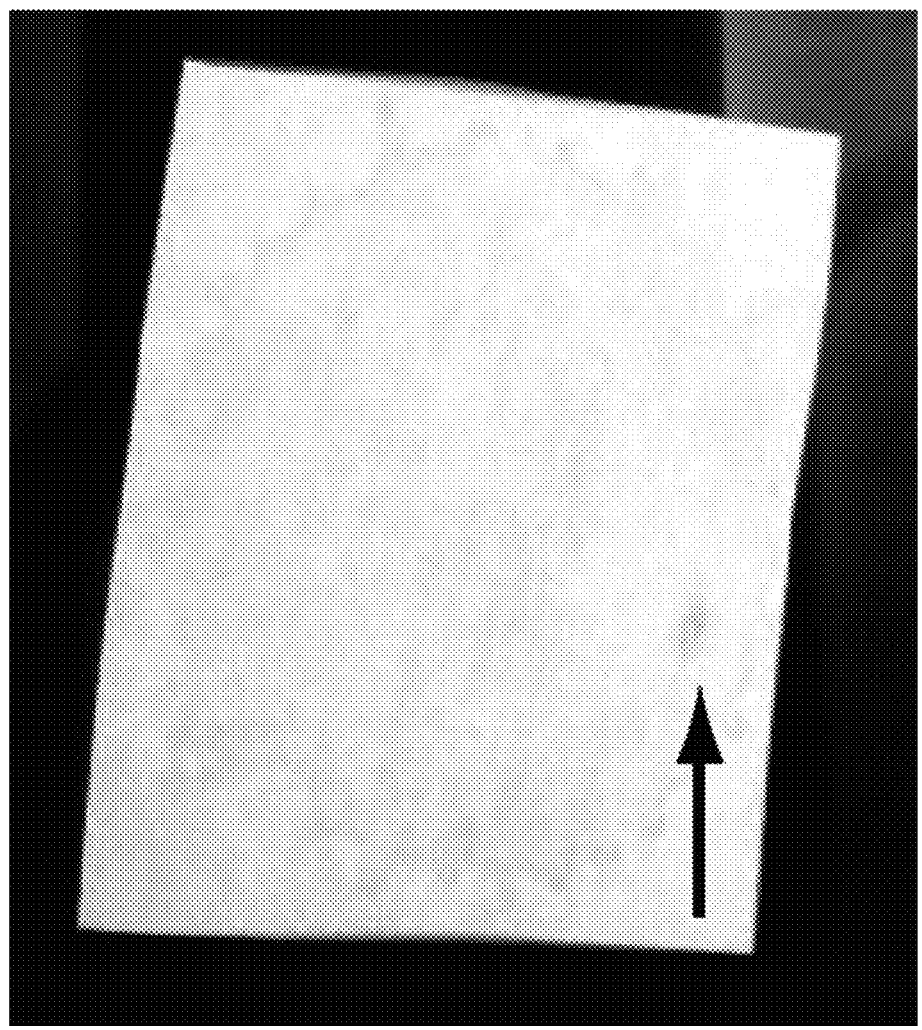
FIG. 7a is a diagram showing glucose production from copy paper by the use of HGcel; the arrow indicates a spot made by a drop of an HGcel enzyme solution.
Figure 7B:
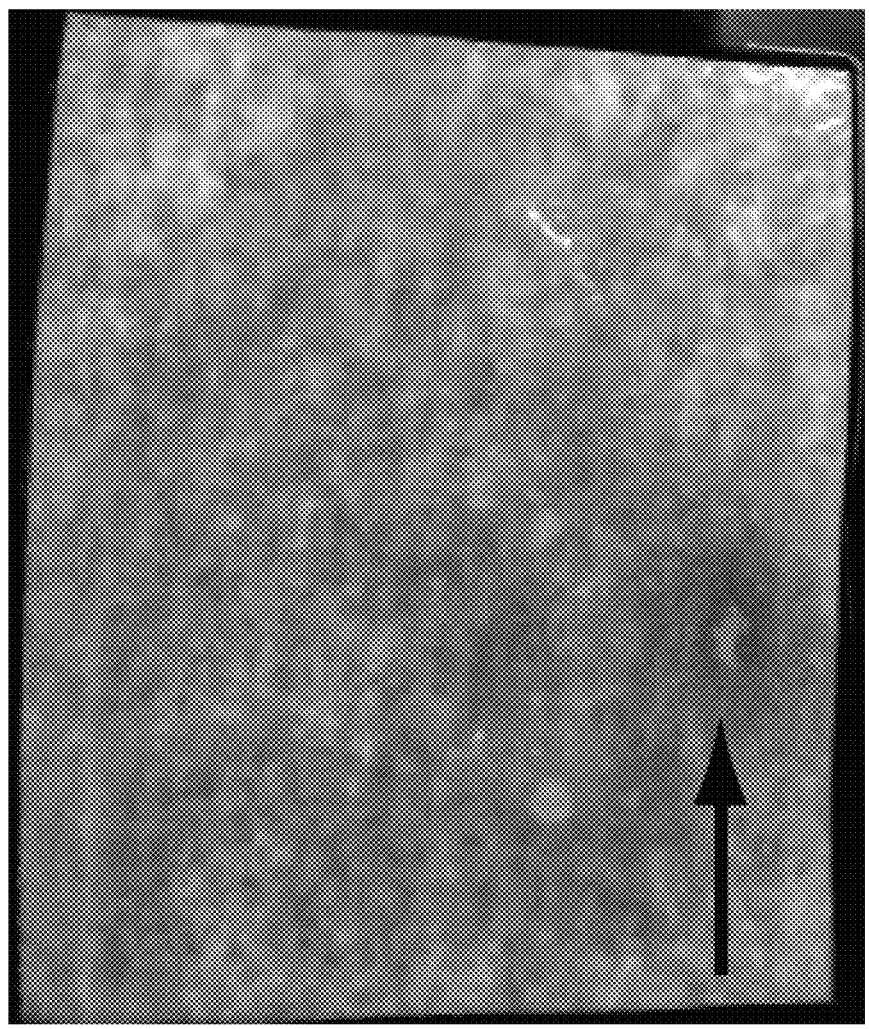
FIG. 7b is a diagram showing glucose production from copy paper by the use of HGcel; the arrow indicates a spot made by a drop of an HGcel enzyme solution, proving that glucose was produced.
Figure 7C:
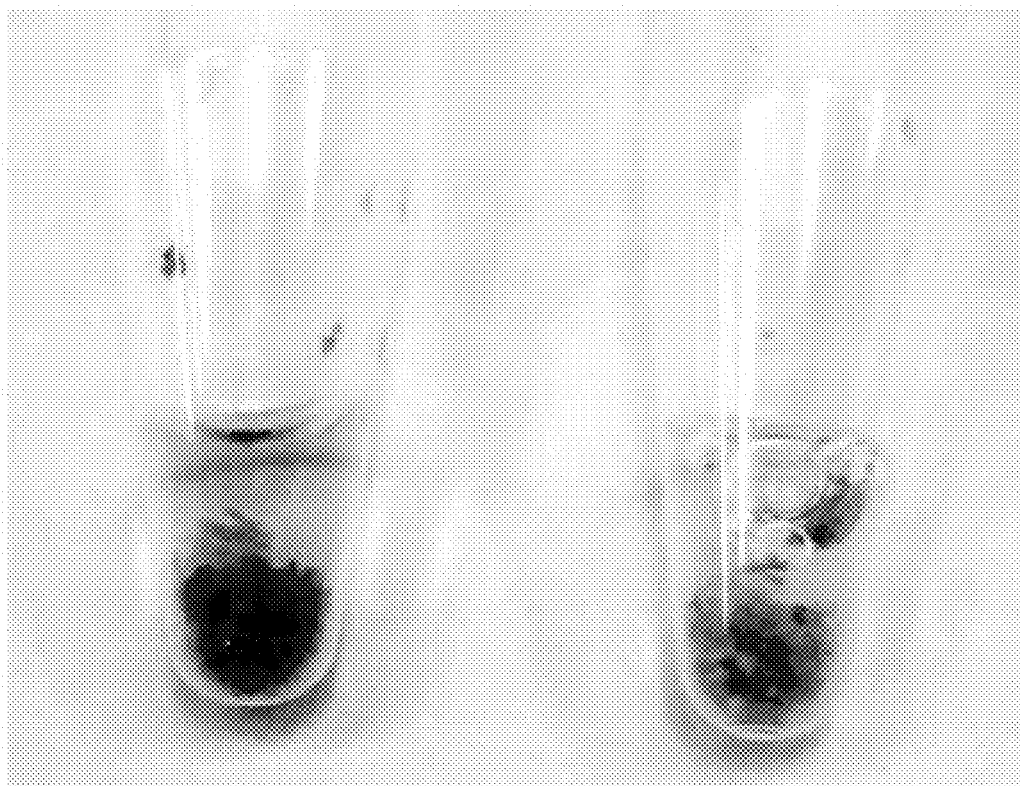
FIG. 7c is a diagram showing glucose production from sawdust by the use of HGcel; the diagram shows that coloring indicating glucose production was not confirmed in the case wherein sawdust was added to a solution not containing HGcel (right vial) while coloring indicating glucose production was confirmed in the case wherein sawdust was added to a solution containing HGcel (left vial).

The amount of glucose produced from a 3.8 mg piece of copy paper with the use of an enzyme preparation solution containing 0.28 U of HGcel was 0.82 μg. Moreover, the HGcel enzyme solution was dropped onto copy paper (See FIG. 7a), and was subjected to hydrolysis reaction at a room temperature (25 degrees Celsius) for 15 hours. It was confirmed that glucose was produced around the dropped area by detecting coloration of pink produced by using the Glucose CII kit reagent (See FIG. 7b). Similarly, sawdust was put into the HGcel enzyme solution, and was subjected to hydrolysis reaction; it was confirmed that a color associated with glucose production was produced (See FIG. 7c). The results proved that glucose can be produced from solid cellulose material by using an enzyme solution containing HGcel.

(8) Acquisition of Base Sequence of HGcel

Based on the information of amino acid sequences disclosed in SEQ ID NO: 5 to 7, mixed-base primers (SEQ ID NO: 12 to 17) were produced. That is, for the amino acid sequence of SEQ ID NO: 5 (TPPMGWLAWER), Primer 211-F (ACNCCNCCNATGGGNTGGYTNGCNTGGGA: SEQ ID NO: 12) and Primer 211-R (TCCCANGCNARCCANCCCATNGGNGGNGT: SEQ ID NO: 13) were synthesized; for the amino acid sequence of SEQ ID NO: 6 (SQMALWAIMAAPLFMSNDLR), Primer 212-F (ATGGCNYTNTGGGCNATHATGGCNGCNCCNYTNTTYATG: SEQ ID NO: 14) and Primer 212-R (CATRAANARNGGNGCNGCCATDATNGCCCANARNGCCAT: SEQ ID NO: 15) were synthesized; and, for the amino acid sequence of SEQ ID NO: 7 (AVIAVNQDPLGIQGR), Primer 22-F (GCNGTNATHGCNGTNAAYCARGAYCCNYTNGGNATHCARGG: SEQ ID NO: 16) and Primer 22-R (CCYTGDATNCCNARNGGRTCYTGRTTNACNGCDATNACNGC: SEQ ID NO: 17) were synthesized.

Then, all RNAs were obtained from deep-sea gammaridean amphipods, and cDNAs were created by using the SMARTer cDNA synthesis kit of Clontech. With the created cDNAs as templates, PCR was carried out by using mixed-base primers and dT20, and TA cloning was performed, and the gene sequences of clones obtained were determined and selected. The resultant base sequence was the base sequence disclosed in SEQ ID NO: 11. Part of the base sequence disclosed in SEQ ID NO: 11 that was estimated to be a gammaridean amphipod-derived base sequence was the base sequence disclosed in SEQ ID NO: 8. The obtained base sequence was part of the cellulase gene, and the mature sequence was estimated to be about 2 kb on the basis of the molecular weight thereof.

INDUSTRIAL APPLICABILITY

Cellulose is one type of hydrocarbon that is the most abundant on the earth. Cellulose is expected to be used as a raw material for producing bioethanol. In order to use cellulose as a raw material for bioethanol, cellulose needs to be converted in advance into glucose. According to the conventional technique, the conversion was performed with three types of hydrolytic enzymes. Moreover, it was difficult to subject natural cellulose without any process to enzymatic treatment.

However, the cellulase of the present invention is able to transform natural cellulose into glucose without using any enzyme other than the cellulase of the present invention. Therefore, the cellulase of the present invention is an effective enzyme for industrial production of bioethanol.

The invention claimed is:

1. A method of producing glucose, comprising a step of producing glucose as a main product by contacting a cellulase with crystalline cellulose and/or non-crystalline cellulose,
wherein the cellulase has an exo-cellulase activity to produce glucose as a main product by hydrolyzing crystalline cellulose and is a cellulase isolated from Hirondella gigas.

2. A method of producing alcohol, comprising: a step of producing glucose as a main product by contacting a cellulase with crystalline cellulose and/or non-crystalline cellulose; and a step of producing alcohol by contacting a yeast with the produced glucose,
wherein the cellulase has an exocellulase activity to produce glucose as a main product by hydrolyzing crystalline cellulose and is a cellulase isolated from Hirondella gigas.

3. The method according to claim 1 or 2, wherein the cellulase comprises an amino acid sequence encoded by a base sequence that hybridizes with a base sequence complementary to the base sequence of SEQ ID NO: 8 at 40 to 75 degrees Celsius in the presence of 0.5 to 2.0M NaCl or a base sequence with an identity of 90% or more to SEQ ID NO: 8.

4. The method according to claim 3, wherein the cellulase comprises an amino acid sequence of SEQ ID NO: 5.

5. The method according to claim 3, wherein the cellulase comprises an amino acid sequence of SEQ ID NO: 6.

6. The method according to claim 3, wherein the cellulase comprises an amino acid sequence of SEQ ID NO: 7.

7. The method according to claim 3, wherein the cellulase has an exo-cellulase activity to produce cellobiose as a by-product by hydrolyzing crystalline cellulose.

8. The method according to claim 3, wherein the cellulase has activity to produce glucose as a main product by hydrolyzing non-crystalline cellulose, and an amount of glucose produced by hydrolyzing crystalline cellulose is at least 1/100 in comparison with an amount of glucose produced by hydrolyzing non-crystalline cellulose.

9. The method according to claim 3, wherein the cellulase has activity to produce 1 μg/mL or more of glucose as a main product by hydrolyzing 5% (w/v) sawdust in a sodium acetate buffer solution (pH 5.6) under reaction conditions of 35 degrees Celsius and 5 hours.

10. The method according to claim 3, wherein a molar ratio of glucose, which is a main product, and cellobiose, which is a by-product, is 1.5:1 to 2.5:1.

11. The method according to claim 3, wherein the crystalline cellulose is selected from a group consisting of sawdust, paper, fiber, wood, Avicel, stalk of plants, root of plants, petal of plants, and leaf of plants.

12. The method according to claim 3, wherein the non-crystalline cellulose is selected from a group consisting of carboxymethylcellulose, phosphoric acid swollen cellulose, alkali swollen cellulose, and sodium cellulose xanthate.

13. The method according to claim 3, wherein the cellulase has a molecular weight of 55,000 to 63,000 by SDS-PAGE method.

14. The method according to claim 3, wherein the cellulase has an optimum pH of 5.4 to 5.8.

15. The method according to claim 3, wherein the cellulase has an optimum temperature of 25 to 40 degrees Celsius.

16. The method according to claim 1 or 2, wherein the cellulase comprises an amino acid sequence encoded by a base sequence that hybridizes with a base sequence with an identity of 95% or more to SEQ ID NO: 8.

17. The method according to claim 1 or 2, wherein the cellulase comprises an amino acid sequence encoded by a base sequence that hybridizes with a base sequence with an identity of 98% or more to SEQ ID NO: 8.

18. The method according to claim 1 or 2, wherein the cellulase comprises an amino acid sequence encoded by the base sequence of SEQ ID NO: 8.

* * * * *